United States Patent
Jin et al.

(10) Patent No.: US 12,295,573 B2
(45) Date of Patent: May 13, 2025

(54) STAPLING DEVICE WITH END EFFECTOR HAVING BOTTOM GUIDE MEMBER

(71) Applicant: Covidien LP, Mansfield, MA (US)

(72) Inventors: Tingting Jin, Shanghai (CN); Xiliang Zhang, Shanghai (CN); Zhaokai Wang, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/284,772

(22) PCT Filed: Mar. 31, 2021

(86) PCT No.: PCT/CN2021/084233
§ 371 (c)(1),
(2) Date: Sep. 28, 2023

(87) PCT Pub. No.: WO2022/205025
PCT Pub. Date: Oct. 6, 2022

(65) Prior Publication Data
US 2024/0180551 A1  Jun. 6, 2024

(51) Int. Cl.
*A61B 17/072* (2006.01)

(52) U.S. Cl.
CPC .. *A61B 17/072* (2013.01); *A61B 2017/07221* (2013.01); *A61B 2017/07271* (2013.01); *A61B 2017/07285* (2013.01)

(58) Field of Classification Search
CPC ........ A61B 17/072; A61B 2017/07221; A61B 2017/07271; A61B 2017/07285
See application file for complete search history.

(56) References Cited

U.S. PATENT DOCUMENTS

| | | | |
|---|---|---|---|
| 5,470,006 A * | 11/1995 | Rodak | A61B 17/072 227/176.1 |
| 5,735,445 A * | 4/1998 | Vidal | A61B 17/072 227/176.1 |
| 6,817,508 B1 | 11/2004 | Racenet et al. | |
| 2004/0164123 A1 | 8/2004 | Racenet et al. | |
| 2005/0139636 A1 | 6/2005 | Schwemberger et al. | |
| 2007/0029364 A1* | 2/2007 | Kruszynski | A61B 17/072 227/175.2 |
| 2008/0023523 A1 | 1/2008 | Racenet et al. | |
| 2010/0282820 A1* | 11/2010 | Kasvikis | A61B 17/068 227/181.1 |

(Continued)

FOREIGN PATENT DOCUMENTS

| | | |
|---|---|---|
| CN | 102423267 B | 11/2014 |
| CN | 106923875 A | 7/2017 |

(Continued)

OTHER PUBLICATIONS

International Search Report for Application No. PCT/CN2020/075298 dated Jan. 5, 2022.

(Continued)

*Primary Examiner* — Michelle Lopez

(57) ABSTRACT

A surgical stapling device includes an end effector having a bottom guide member to confine tissue in the path of a cutting member and ensure that tissue is cleanly cut through. The bottom guide member can be supported on an end effector frame and be reusable or supported on the cartridge module and be disposable.

17 Claims, 21 Drawing Sheets

(56) References Cited

U.S. PATENT DOCUMENTS

2018/0153544 A1    6/2018    Maddur Shankarsetty et al.

FOREIGN PATENT DOCUMENTS

| | | |
|---|---|---|
| CN | 108472036 B | 7/2021 |
| EP | 3329862 B1 | 4/2021 |
| JP | 2005-93043 A | 4/2005 |
| JP | 2007-44518 A | 2/2007 |
| WO | 2021022407 A1 | 2/2021 |

OTHER PUBLICATIONS

Written Opinion for Application No. PCT/CN2020/075298 dated Jan. 5, 2022.
Office Action for Japanese Patent Application No. 2023-560518 mailed Dec. 2, 2024, 12 pages.

* cited by examiner

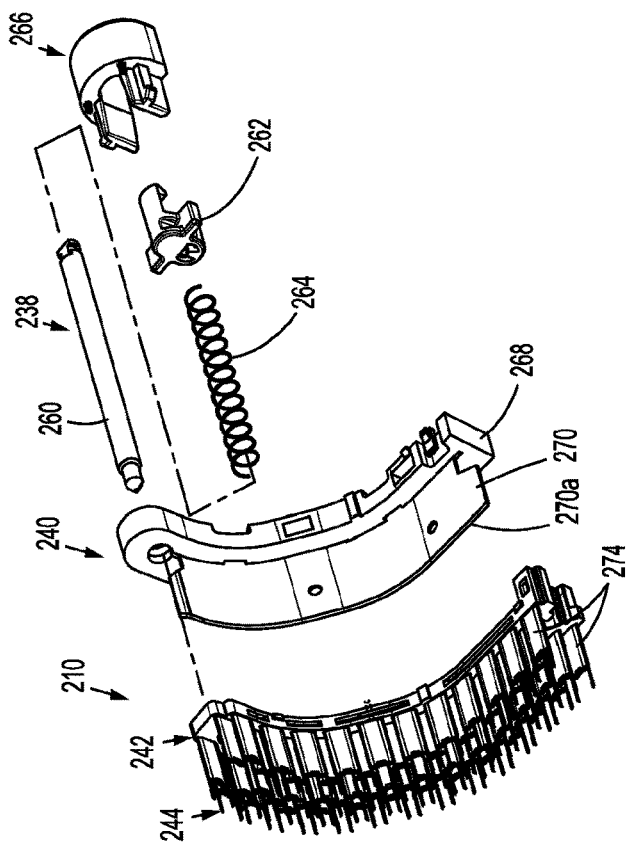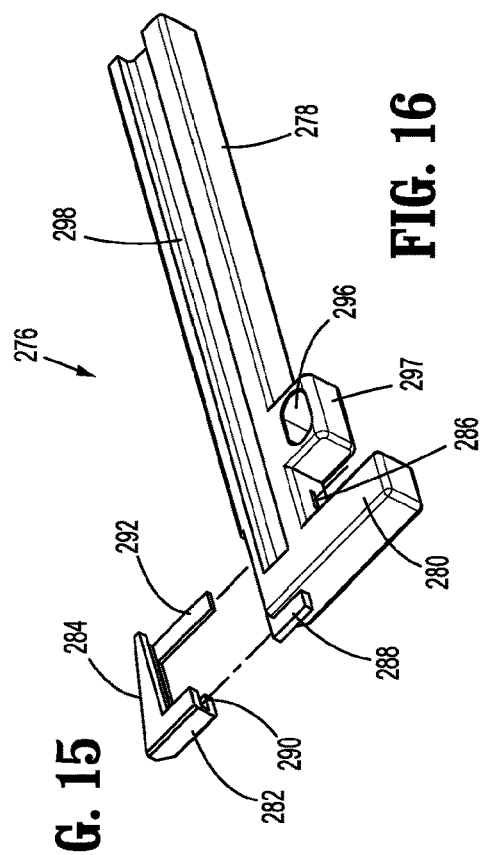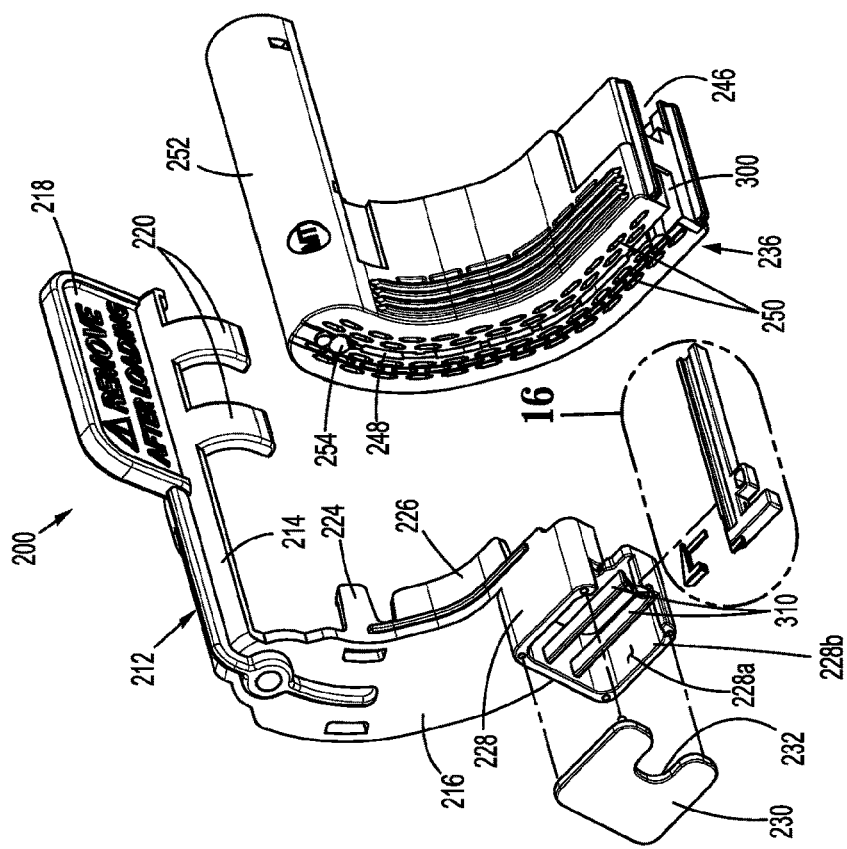
FIG. 15
FIG. 16

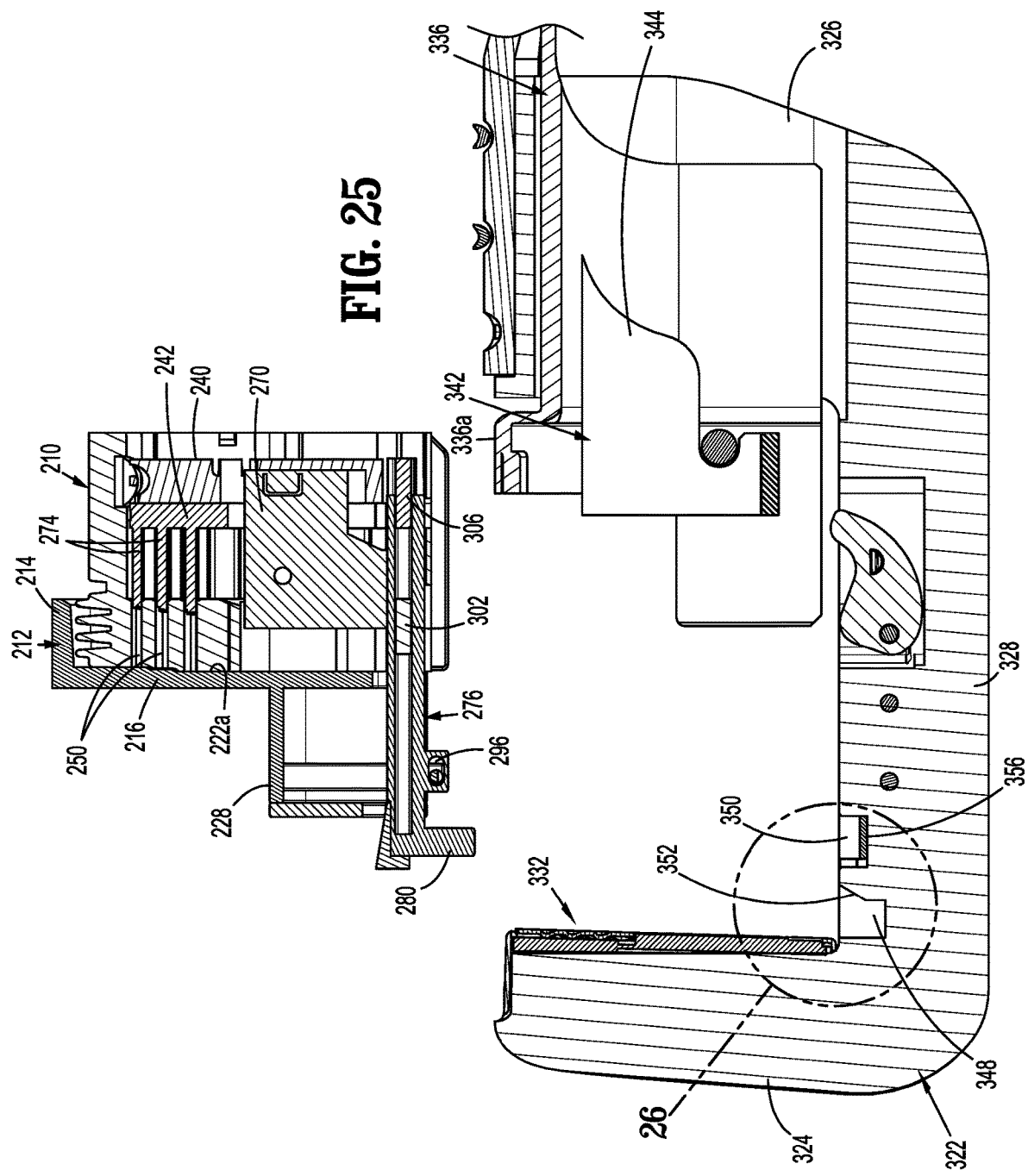

STAPLING DEVICE WITH END EFFECTOR HAVING BOTTOM GUIDE MEMBER

FIELD

The present technology is generally related to surgical stapling devices and, more particularly, to surgical stapling devices that have U-shaped end effectors for capturing tissue.

BACKGROUND

Surgical stapling devices are commonly used during a variety of surgical procedures to expedite dissection and suturing of tissue while minimizing trauma to a patient. Typically, the stapling devices include an end effector that has a cartridge assembly and an anvil assembly. The cartridge assembly and the anvil assembly are movable in relation to each other between open and clamped positions to clamp tissue therebetween. When the tissue is clamped between the cartridge and anvil assemblies, the stapling device can be fired to eject staples from the cartridge assembly into a staple forming surface of the anvil assembly to suture the tissue. The stapling devices often include a knife assembly that has a cutting blade that is advanced from within the cartridge assembly into the anvil assembly to cut the tissue clamped between the cartridge and anvil assemblies.

Surgical stapling devices are available in a variety of types for performing a variety of different surgical procedures. One type of stapling device includes a U-shaped end effector that has a frame having a distal transverse portion, a proximal transverse portion, and a longitudinal portion interconnecting the distal transverse portion and the proximal transverse portion. Each of the distal and proximal transverse portions has a first end coupled to the longitudinal portion and a second end spaced from the longitudinal portion. The second ends of the distal and proximal transverse portions define an opening for receiving tissue. The anvil assembly is supported on the distal transverse portion which extends from the longitudinal portion in cantilevered fashion. The cartridge assembly is supported adjacent the proximal transverse portion and is movable towards the distal transverse portion to move the anvil and cartridge assemblies into juxtaposed alignment and clamp tissue between the anvil and cartridge assemblies.

Some stapling devices include an alignment pin that is movable from within the cartridge assembly into the anvil assembly to close the opening defined between the second ends of the distal and proximal transverse portions of the frame to trap tissue between the anvil and cartridge assemblies in a position to be transected or resected by the cutting blade. Other stapling devices also include a bottom pin or guide member that is positioned adjacent the first ends of the distal and proximal transverse portions to interface with the cutting blade and improve the cutting capabilities of the stapling device especially at an end or bottom of the cartridge assembly adjacent the longitudinal portion of the frame.

A continuing need exists in the art for an end effector with improved cutting capabilities along the bottom of the cartridge assembly.

SUMMARY

This disclosure is directed to a surgical stapling device that includes an end effector having a bottom guide member to confine tissue in the path of a cutting member to ensure that tissue is cleanly cut through. The bottom guide member can be supported on an end effector frame of the end effector such that the guide member is reusable or supported on the cartridge module of the end effector such that the guide member is disposable with the cartridge module.

Aspects of this disclosure are directed to a stapling device that includes an elongate body, a clamp slide assembly, a thrust bar, and an end effector including a cartridge module, an anvil, an end effector frame, and a guide assembly. The elongate body has a proximal portion and a distal portion. The clamp slide assembly has a distal portion that defines a pocket and is movable between retracted and advanced positions. The thrust bar has a proximal portion and a distal portion. The cartridge module of the end effector is releasably received within the pocket of the clamp slide assembly and includes a cartridge body, a knife assembly, a pusher, and staples. The cartridge body defines a knife slot and staple receiving slots positioned on each side of the knife slot. Each of the staple receiving slots receives one of the staples. The knife assembly includes a knife holder and a cutting blade. The pusher includes fingers that are received in the staple receiving slots. The knife assembly and the pusher are movable within the cavity of the cartridge body from retracted to advanced positions to eject the staples from the cartridge body and to advance the cutting blade from a position recessed within the cartridge body to a position extending from the knife slot of the cartridge body. The end effector frame has a distal transverse portion, a proximal transverse portion, and a longitudinal portion interconnecting the distal and proximal transverse portions at spaced locations to define a recess that receives the distal portion of the clamp slide assembly and the distal portion of the thrust bar. The longitudinal portion of the end effector frame has an inwardly facing surface that defines a channel that extends longitudinally along the inwardly facing surface. The anvil is supported on the distal transverse portion of the end effector frame. The guide assembly is supported on the longitudinal portion of the end effector frame and includes a guide member having a body. The body includes a lower portion and a guide portion that extends distally of the lower portion. The lower portion is received within the channel of the longitudinal portion of the end effector frame. The body defines a recess that is defined in part by an abutment surface that is aligned with the cutting blade. The guide member is movable from a retracted position to an advanced position in response to movement of the knife assembly from its retracted position to its advanced position.

Other aspects of this disclosure are directed to an end effector including an end effector frame and a guide assembly. The end effector frame includes a distal transverse portion, a proximal transverse portion, and a longitudinal portion interconnecting the distal and proximal transverse portions at spaced locations to define a recess. The longitudinal portion of the end effector frame has an inwardly facing surface that defines a channel that extends longitudinally along the inwardly facing surface. The guide assembly is supported on the longitudinal portion of the end effector frame and includes a guide member having a body that has a lower portion and a guide portion that extends distally of the lower portion. The lower portion is received within the channel in the longitudinal portion of the end effector frame. The body defines a recess that is defined in part by an abutment surface that is aligned with a cutting blade of a cartridge module. The guide member is movable from a retracted position to an advanced position along the longitudinal portion of the end effector frame.

In aspects of the disclosure, the guide assembly includes a biasing member that urges the guide member towards its retracted position.

In some aspects of the disclosure, the distal transverse portion defines a bore that receives the guide portion of the guide member.

In certain aspects of the disclosure, the biasing member is received within the bore in the distal transverse portion of the end effector frame.

In aspects of the disclosure, the guide portion of the guide member includes a rectangular portion and a cylindrical portion that extends distally from the rectangular portion, and the biasing member is positioned about the cylindrical portion and is engaged with the rectangular portion.

In some aspects of the disclosure, the thrust bar is configured to couple to the knife holder when the cartridge module is loaded onto the clamp slide assembly.

In certain aspects of the disclosure, the cartridge module and the end effector frame have curved configurations.

In aspects of the disclosure, the lower portion of the guide member defines a longitudinal slot and the longitudinal portion of the end effector frame supports a pin that extends across the channel in the longitudinal portion and through the longitudinal slot in the lower portion of the guide member.

In some aspects of the disclosure, the stapling device includes a handle assembly, and the elongate body extends distally from the handle assembly.

Other aspects of this disclosure are directed to a surgical stapling device including an elongate body, a clamp slide assembly, a thrust bar, an end effector frame, an anvil, a reload assembly, and a guide assembly. The elongate body has a proximal portion and a distal portion. The clamp slide assembly has a distal portion that defines a pocket and is movable between retracted and advanced positions. The thrust bar has a proximal portion and a distal portion. The end effector frame has a distal transverse portion, a proximal transverse portion, and a longitudinal portion interconnecting the distal and proximal transverse portions. The distal and proximal transverse portions are spaced from each other to define a recess that receives the distal portion of the clamp slide assembly and the distal portion of the thrust bar. The longitudinal portion of the end effector frame has an inwardly facing surface that defines a distal bore that is defined in part by an angled camming surface. The anvil is supported on the distal transverse portion of the end effector frame. The reload assembly includes a cartridge module and a shipping cap. The cartridge module includes a cartridge body, a knife assembly, a pusher, staples, and a guide assembly. The cartridge body defines a knife slot, staple receiving slots positioned on each side of the knife slot, and a channel. Each of the staple receiving slots receives one of the staples. The knife assembly includes a knife holder and a cutting blade. The pusher includes fingers that are received in the staple receiving slots. The knife assembly and the pusher are movable within the cavity of the cartridge body from retracted to advanced positions to eject the staples from the cartridge body and to advance the cutting blade from a position recessed within the cartridge body to a position extending from the knife slot of the cartridge body. The cartridge module is releasably received within the pocket of the clamp slide assembly. The guide assembly includes a guide member that is received within the channel of the cartridge body and is movable from a retracted position to an advanced position. The guide member includes an elongate body portion and a finger extending downwardly from the elongate body portion. The finger is positioned to engage the angled camming surface on the longitudinal portion of the end effector frame when the cartridge module is loaded onto the clamp slide assembly to move the guide member from its retracted position to its advanced position. The shipping cap is releasably supported on the cartridge module.

In aspects of the disclosure, the guide assembly includes a biasing member that is positioned to urge the guide member to its retracted position.

In some aspects of the disclosure, the elongate body portion of the guide member includes an extension that extends downwardly from the elongate body portion and defines an elongate opening, and the shipping cap includes flexible arms.

In certain aspects of the disclosure, each of the flexible arms includes a protrusion that is received within the opening in the extension to releasably secure the shipping cap to the cartridge module.

In aspects of the disclosure, the longitudinal portion of the end effector frame defines a proximal bore that receives an insert plate, and the flexible arms are positioned to engage the insert plate when the cartridge module is loaded onto the clamp slide assembly to cam the flexible arms outwardly and remove the protrusions from the opening in the extension to facilitate removal of the shipping cap from the cartridge module.

Other features of the disclosure will be appreciated from the following description.

BRIEF DESCRIPTION OF THE DRAWINGS

Various aspects of the disclosure are described herein below with reference to the drawings, wherein:

FIG. 15 is an exploded side perspective view of the reload assembly shown in FIG. 14;

FIG. 16 is a side perspective view from the distal end of a guide member of the reload assembly shown in FIG. 15 with parts separated;

FIG. 24 is a cross-sectional view taken along section line 24-24 of FIG. 23;

FIG. 25 is a cross-sectional view taken along section line 25-25 of FIG. 22;

DETAILED DESCRIPTION

Figure 1:
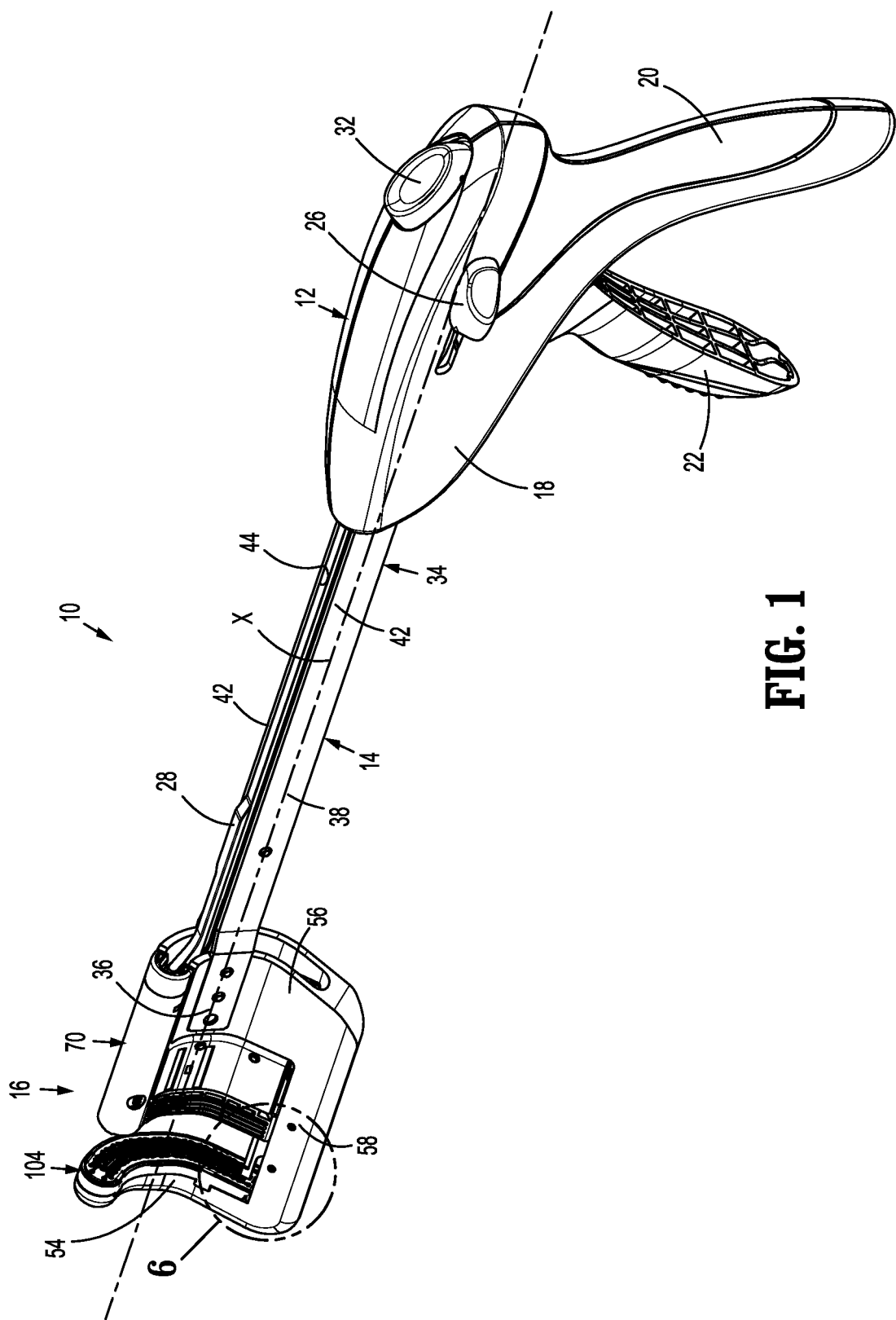
FIG. 1 is a side perspective view of a stapling device including an end effector according to aspects of the disclosure with the end effector in a pre-fired open position.

The disclosed surgical stapling devices will now be described in detail with reference to the drawings in which like reference numerals designate identical or corresponding elements in each of the several views. However, it is to be understood that the aspects of the disclosure are merely exemplary and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device in its customary manner, while the term "distal" is used generally to refer to that portion of the device that is farther from the clinician during use of the device in its customary manner. In addition, the term "clinician" is used generally to refer to medical personnel including doctors, nurses, and support personnel. In addition, directional terms such as front, rear, upper, lower, top, bottom, and similar terms are used to assist in understanding the description and are not intended to limit the disclosure.

FIG. 1 illustrates the disclosed surgical stapling device shown generally as stapling device 10. The stapling device 10 includes a handle assembly 12, an elongate body 14 that extends distally from the handle assembly 12, and an end effector 16 that is supported on a distal portion of the elongate body 14. The elongate body 14 defines a longitudinal axis "X". The handle assembly 12 includes a housing 18 that defines a stationary handle 20 and supports a movable trigger 22. In aspects of the disclosure, the movable trigger 22 is supported by the housing 18 to pivot in relation to the stationary handle 20 between non-actuated and actuated positions to operate the end effector 16. The handle assembly 12 also supports buttons 26 (only one is shown) that are positioned on each side of the housing 18 and are movable along the housing 18 to advance and retract an alignment pin pusher 28. The alignment pin pusher 28 is positioned and configured to engage an alignment pin 30 (FIG. 2) within the end effector 16 to move the alignment pin 30 between retracted and advanced positions. The handle assembly 12 also includes a release button 32 that can be depressed to move the end effector 16 from a clamped position to an unclamped position. For a more detailed description of a suitable handle assembly 12, see, e.g., U.S. Pat. No. 6,817,508 ("the '508 patent").

The stapling device 10 includes a frame 34 that extends from within the handle assembly 12 to the end effector 16. The frame 34 includes a distal portion 36 that supports the end effector 16 and a proximal portion (not shown) that is supported within the housing 18 of the handle assembly 12. The frame 34 includes a central portion 38 that includes spaced frame members 42 that define an elongate channel 44 that extends between the handle assembly 12 and the end effector 16. The elongate body 14 includes supports a clamp slide assembly 48 (FIG. 2), a thrust bar 50, and the alignment pin pusher 28 which are received within the channel 44 defined by the frame members 42 of the stapling device 10 and moved between retracted and advanced positions within the channel 44.

Figure 2:
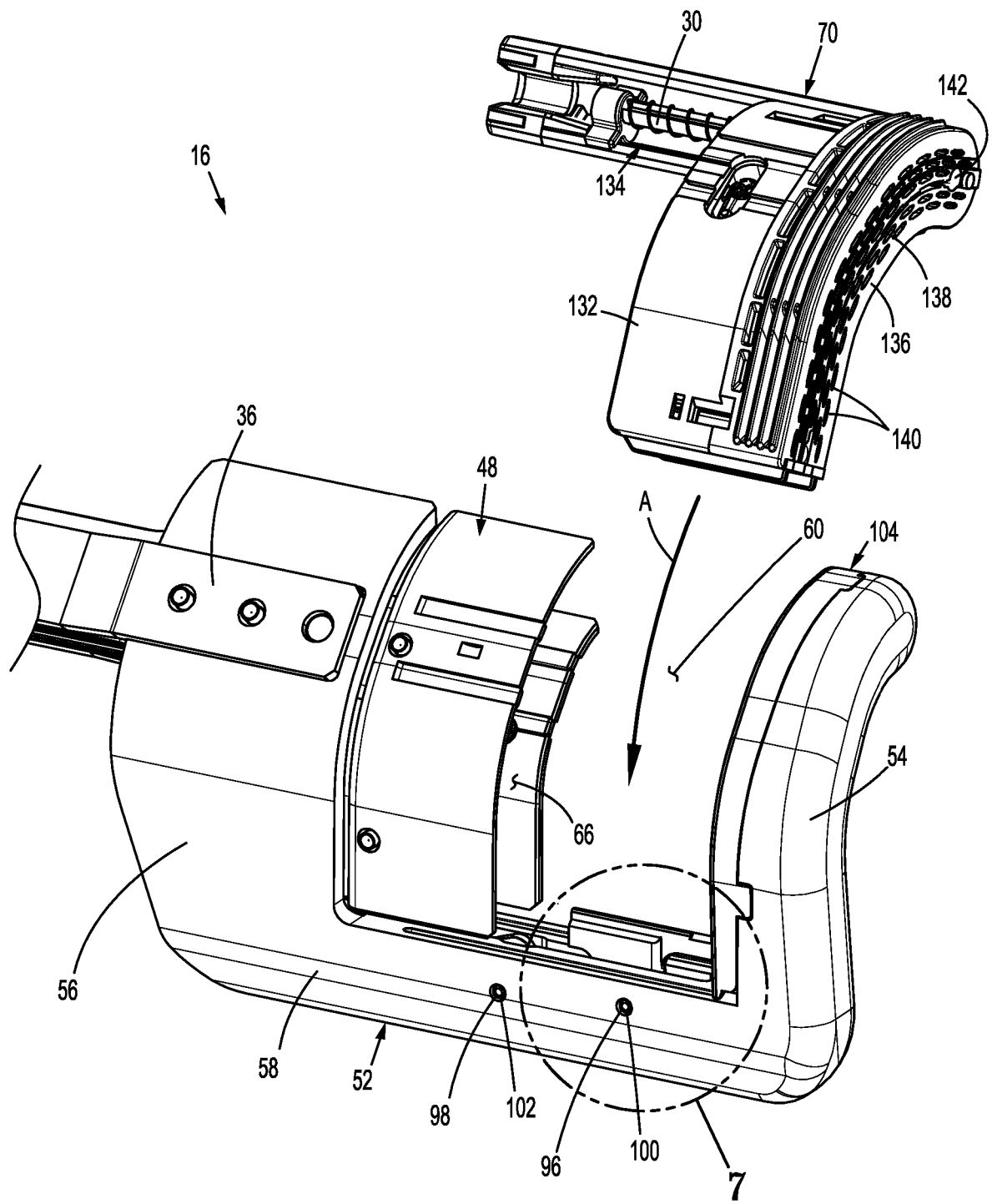
FIG. 2 is side perspective view of an end effector of the stapling device shown in FIG. 1 with a cartridge module of the end effector removed from a clamp slide assembly of the stapling device.
Figure 3:
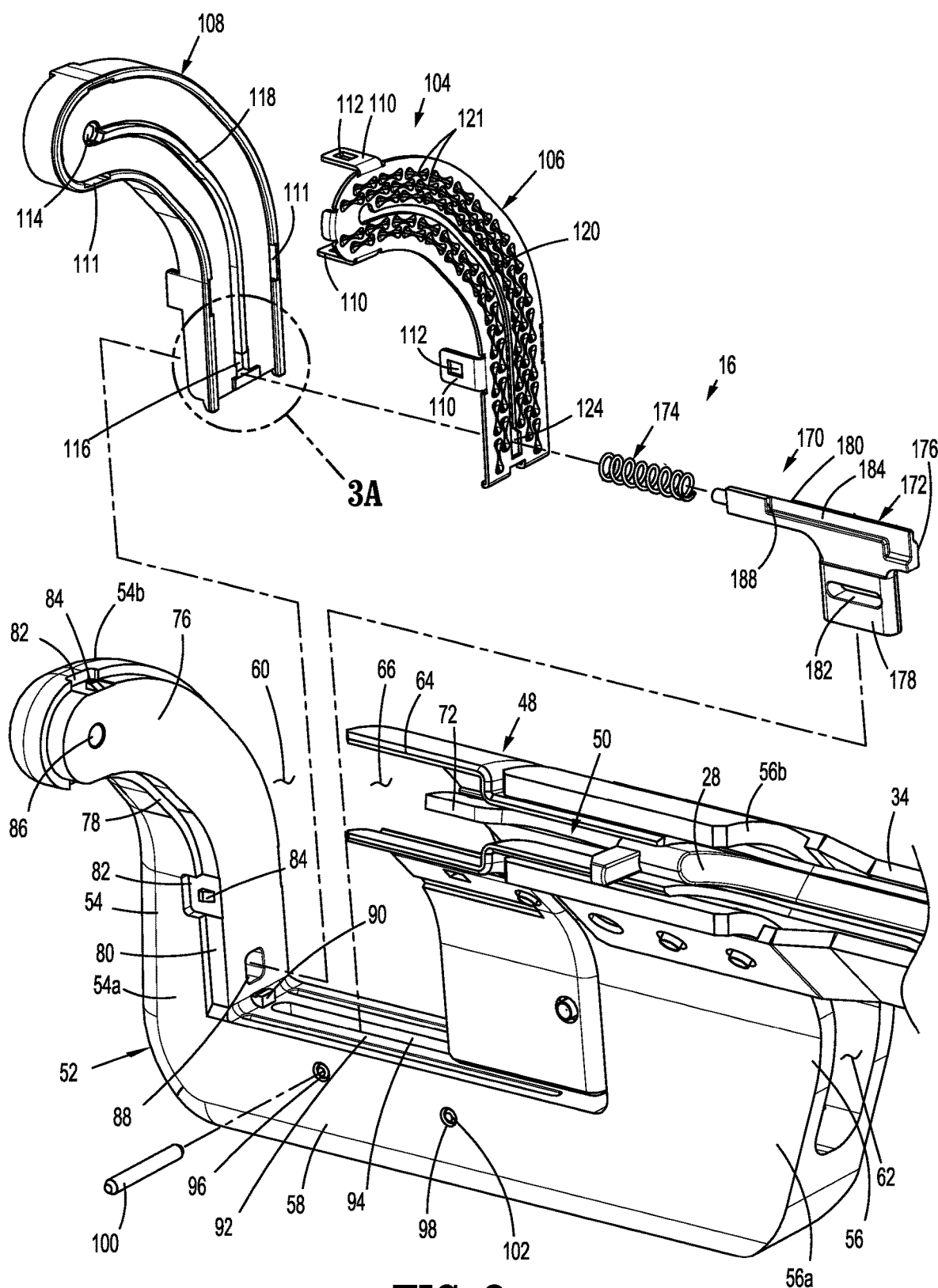
FIG. 3 is a side perspective exploded view of the end effector of the stapling device shown in FIG. 1.
Figure 3A:
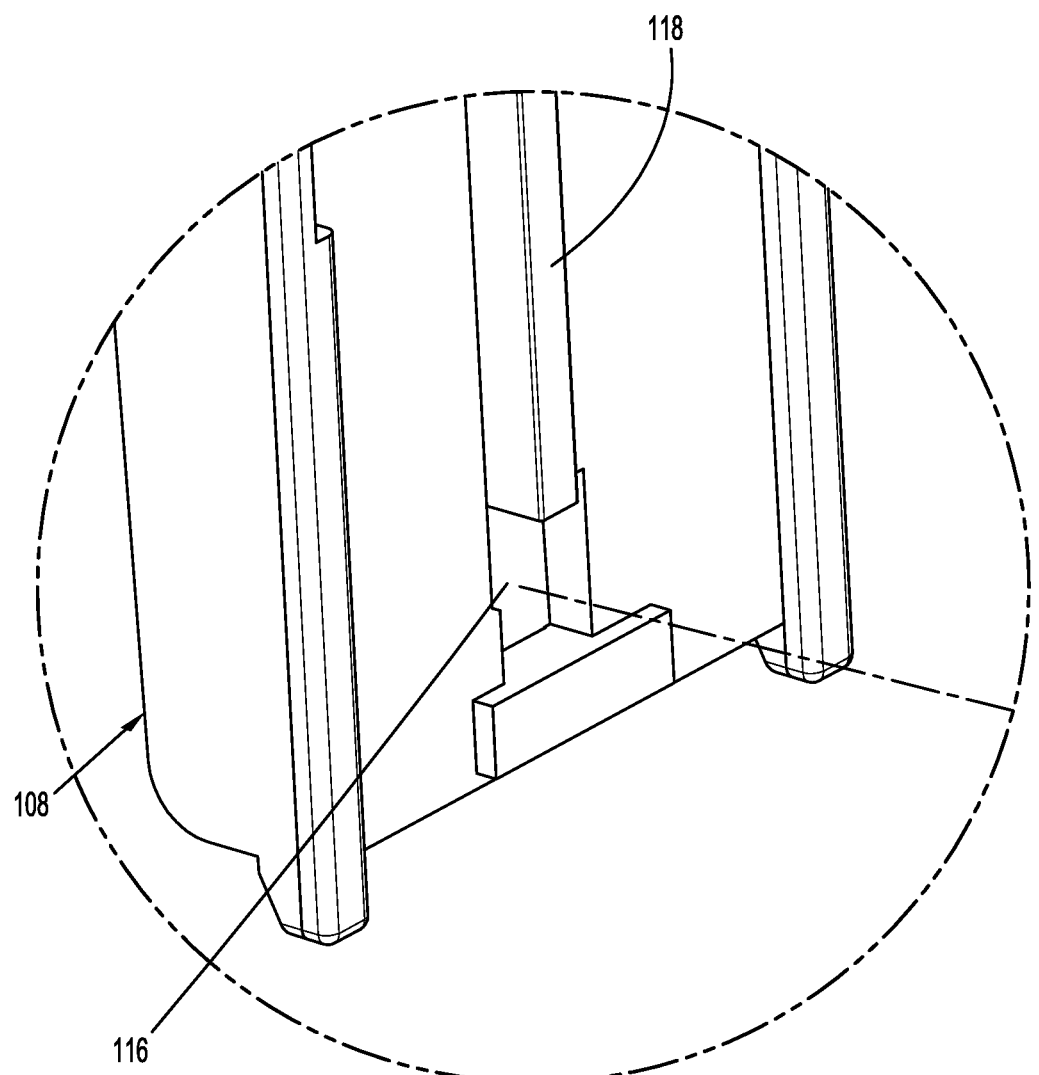
FIG. 3A is an enlarged view of the indicated area of detail shown in FIG. 3.

FIGS. 2 and 3 illustrate the end effector 16 of the stapling device 10 and includes an end effector frame 52 that has a U-shaped configuration and includes a distal transverse portion 54, a proximal transverse portion 56, and a longitudinal portion 58 that interconnects the distal transverse portion 54 and the proximal transverse portion 56. The distal and proximal transverse portions 54 and 56 are spaced from each other to define a recess 60 that is positioned between the distal and proximal transverse portions 54 and 56. In some aspects of the disclosure, the distal and proximal transverse portions 54 and 56 are curved along axes transverse to the longitudinal axis "X" of the elongate body 14 of the stapling device 10. Alternately, the distal and proximal transverse portions may be linear or comprised of a plurality of linear portions that are positioned at angles in relation to each other.

Each of the distal and proximal transverse portions 54 and 56 has a first end 54a,56a, respectively, that is coupled to (e.g., formed with) the longitudinal portion 58 of the end effector frame 52 and a second end 54b, 56b, respectively, that is spaced from the longitudinal portion 58 of end effector frame 52. The second end 56b of the proximal transverse portion 56 of the end effector frame 52 is coupled to the frame 34 of the elongate body 14 of the stapling device 10. The second end 54b of the distal transverse portion 54 of the end effector frame 52 is spaced from the longitudinal portion 58 such that the distal transverse portion 54 is supported on the longitudinal portion 58 in cantilevered fashion. The proximal transverse portion 56 defines a transverse slot 62 that facilitates passage of the clamp slide assembly 48 and the thrust bar 50 through the frame 34 into the recess 60.

The clamp slide assembly 48 includes a distal portion 64 (FIG. 3) that defines a curved pocket 66 (FIG. 3) that is configured to receive a replaceable cartridge module 70 (FIG. 2). The distal portion 64 of the clamp slide assembly 48 is positioned distally of the proximal transverse portion 56 of the end effector frame 52 within the recess 60 of the end effector frame 52. The clamp slide assembly 48 is movable between retracted and advanced positions to move the cartridge module 70 within the recess 60 defined by the end effector frame 52 between spaced and clamped positions as described in further detail below.

Figure 9:
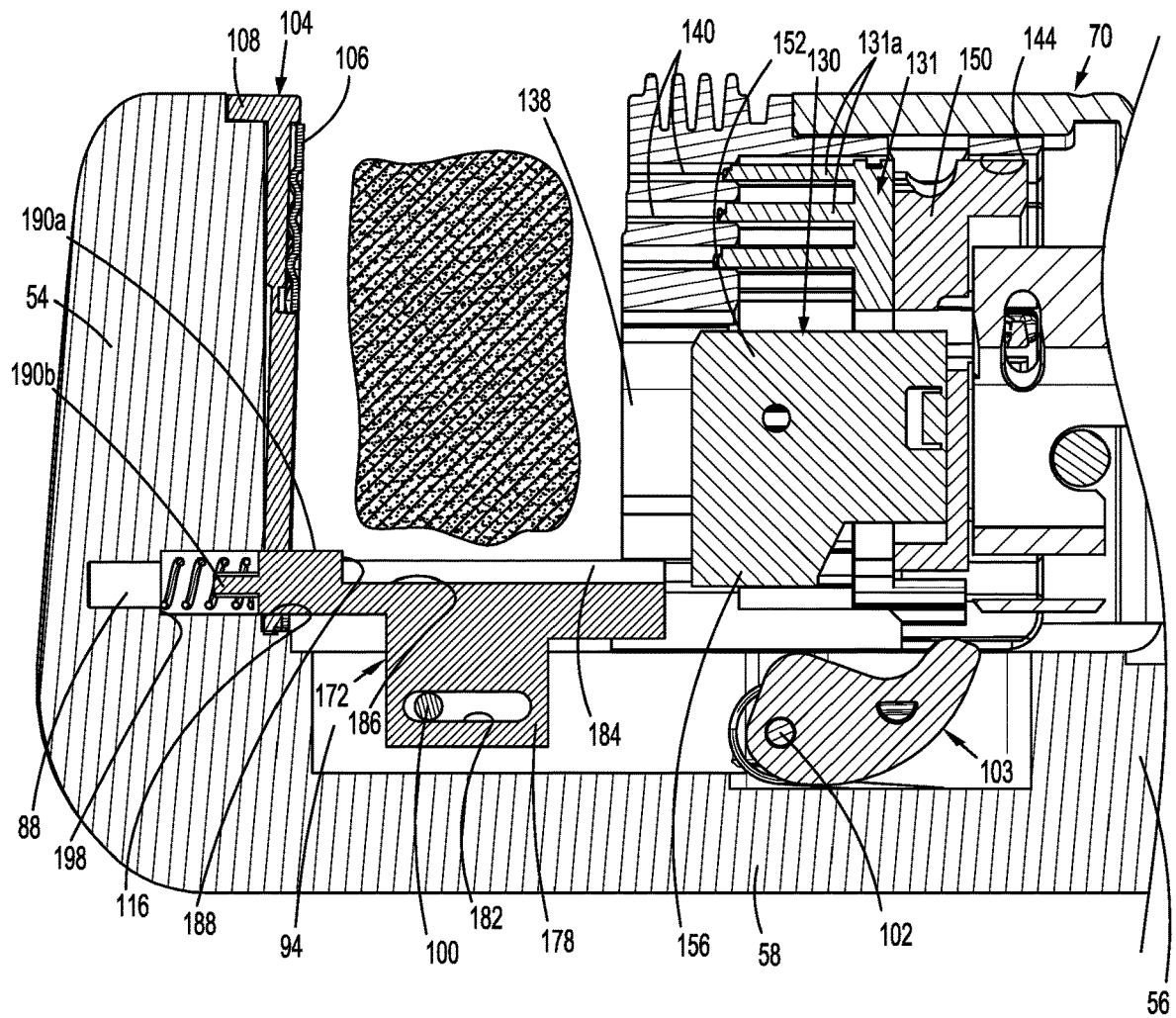
FIG. 9 is a cross-sectional view taken along section line 9-9 of FIG. 8.

The thrust bar 50 includes a distal portion 72 that is positioned within the curved pocket 66 defined by the distal portion 64 of the clamp slide assembly 48. When the cartridge module 70 (FIG. 2) is inserted into the curved pocket 66 of the clamp slide assembly 48 in the direction indicated by arrow "A" in FIG. 2, the distal portion 72 of the thrust bar 50 engages a knife assembly 130 (FIG. 4) of the cartridge module 70 such that movement of the thrust bar 50 from its retracted position to its advanced position advances the knife assembly 130 and a pusher 131 (FIG. 9) to eject staples from the cartridge module 70 and cut tissue.

FIG. 3 illustrates the distal transverse portion 54 of the end effector frame 52 which includes a transverse proximal support surface 76, a shoulder 78 that is positioned about the support surface 76, and a side wall 80 that extends between the support surface 76 and the shoulder 78. The side wall 80 defines cutouts 82 and includes tabs 84 positioned within the cutouts 82. The distal transverse portion 54 defines an alignment pin bore 86 and a bottom guide bore 88 that are formed in the support surface 76 and includes an alignment protrusion 90 that is positioned adjacent the support surface 76 and the longitudinal portion 58 of the end effector frame 52.

The longitudinal portion 58 of the end effector frame 52 includes an inner surface 92 that faces the recess 60. A channel 94 is formed in the longitudinal portion 58 of the end effector frame 52. The channel 94 extends longitudinally along the inner surface 92 between the distal and proximal transverse portions 54 and 56 of the end effector frame 52. The longitudinal portion 58 of the end effector frame 52 also defines transverse bores 96 and 98. The transverse bore 96 extends across the channel 94 and receives a pin 100 and the transverse bore 98 receives a pin 102. The pin 102 supports a lockout member 103 (FIG. 9) which is described in further detail in the '508 patent and will not be described in further detail herein.

The distal transverse portion 54 of the end effector frame 52 supports an anvil assembly 104 that includes an anvil member 106 and a cut plate 108. The cut plate 108 is received on the support surface 76 (FIG. 3) of the distal transverse portion 54 of the end effector frame 52 and the anvil member 106 is positioned on top of the cut plate 108 to sandwich the cut plate 108 on the distal transverse portion 54 of the end effector frame 52. The anvil member 106 includes distally extending brackets 110 that extend through openings 111 in the cut plate 108 and are received within the cutouts 82 formed in the side wall 80 of the distal transverse portion 54 of the end effector frame 52. Each of the brackets 110 defines an opening 112 that receives one of the tabs 84 on the side wall 80 of the distal transverse portion 54 of the end effector frame 52 to secure the anvil member 106 and the cut plate 108 to the distal transverse portion 54 of the end effector frame 52. Receipt of the brackets 110 through the openings 111 in the cut plate 108 and in the cutouts 82 in the distal transverse portion 52 of the end effector frame 52 properly aligns the anvil assembly 104 on the distal transverse portion 52 of the end effector frame 52.

The cut plate 108 defines an alignment pin opening 114 and a guide member opening 116 that are positioned on opposite end portions of the cut plate 108. The cut plate 108 also includes a proximally extending rib 118. The anvil member 106 defines staple forming pockets 121, a knife slot 120, an alignment pin opening 122, and a guide member opening 124. The knife slot 120 receives the proximally extending rib 118 when the anvil assembly 104 is assembled onto the distal transverse portion 54 of the end effector frame 52.

FIG. 2 illustrates the cartridge module 70 which includes a module body 132, an alignment pin assembly 134, the knife assembly 130 (FIG. 4), the pusher 131, and staples (not shown). The module body 132 includes a distal surface 136 that is positioned to engage and clamp tissue against the anvil assembly 104 when the cartridge module 70 is moved to its advanced or clamped position within the recess 60 of the end effector frame 52. The module body 132 defines a knife slot 138, staple receiving slots 140 that are positioned on opposite sides of the knife slot 138, and an alignment pin bore 142. Each of the staple receiving slots 140 receives a staple (not shown). The module body 132 defines a cavity 144 (FIG. 9) that receives the knife assembly 130 and the pusher 131 to allow movement of the knife assembly 130 and pusher 131 between retracted and advanced positions. The pusher 131 defines a knife slot (not shown) and includes fingers 131a that are received in the staple receiving slots 140 such that movement of the pusher from its retracted position to its advanced position ejects the staples from the module body 132.

Figure 4:
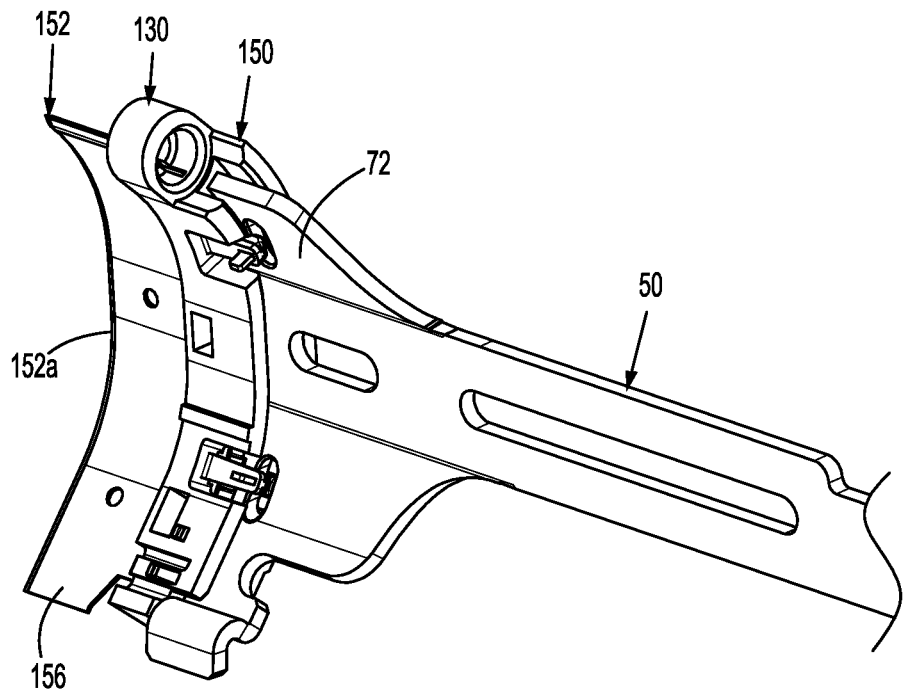
FIG. 4 is a side perspective view of a thrust bar of the stapling device shown in FIG. 1 and a knife assembly of the cartridge module shown in FIG. 3 with the knife assembly coupled to the thrust bar.
Figure 5:
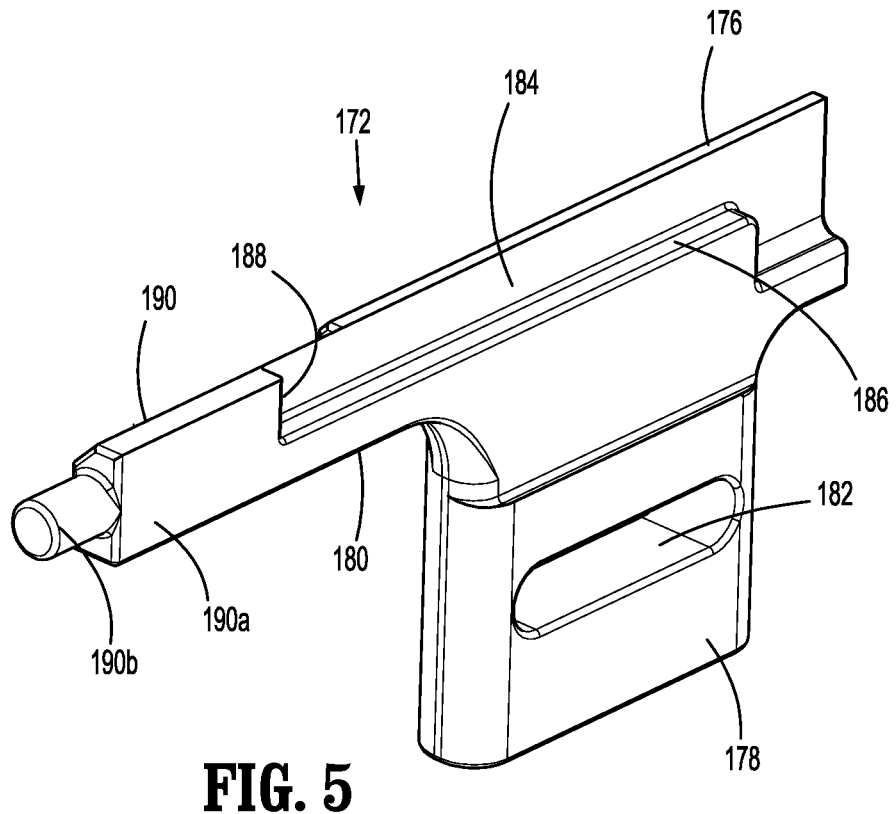
FIG. 5 is a side perspective view of a guide member of a guide assembly of the end effector shown in FIG. 3.
Figure 6:
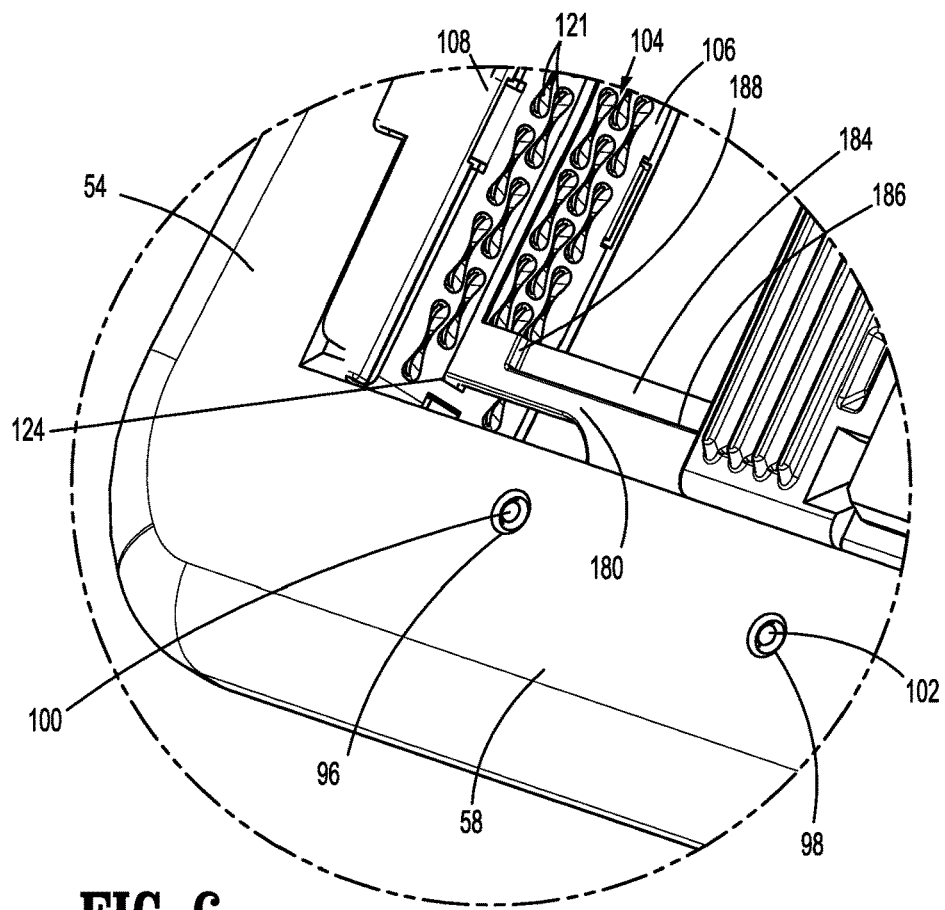
FIG. 6 is an enlarged view of the indicated area of detail shown in FIG. 1.
Figure 7:
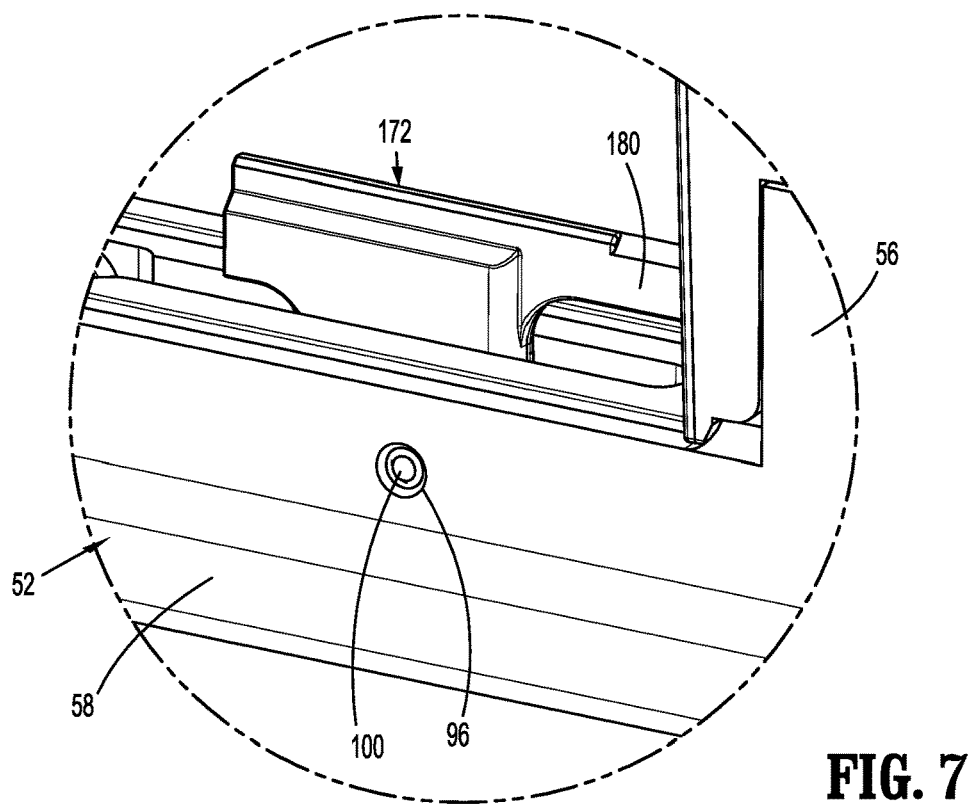
FIG. 7 is an enlarged view of the indicated area of detail shown in FIG. 2.
Figure 8:
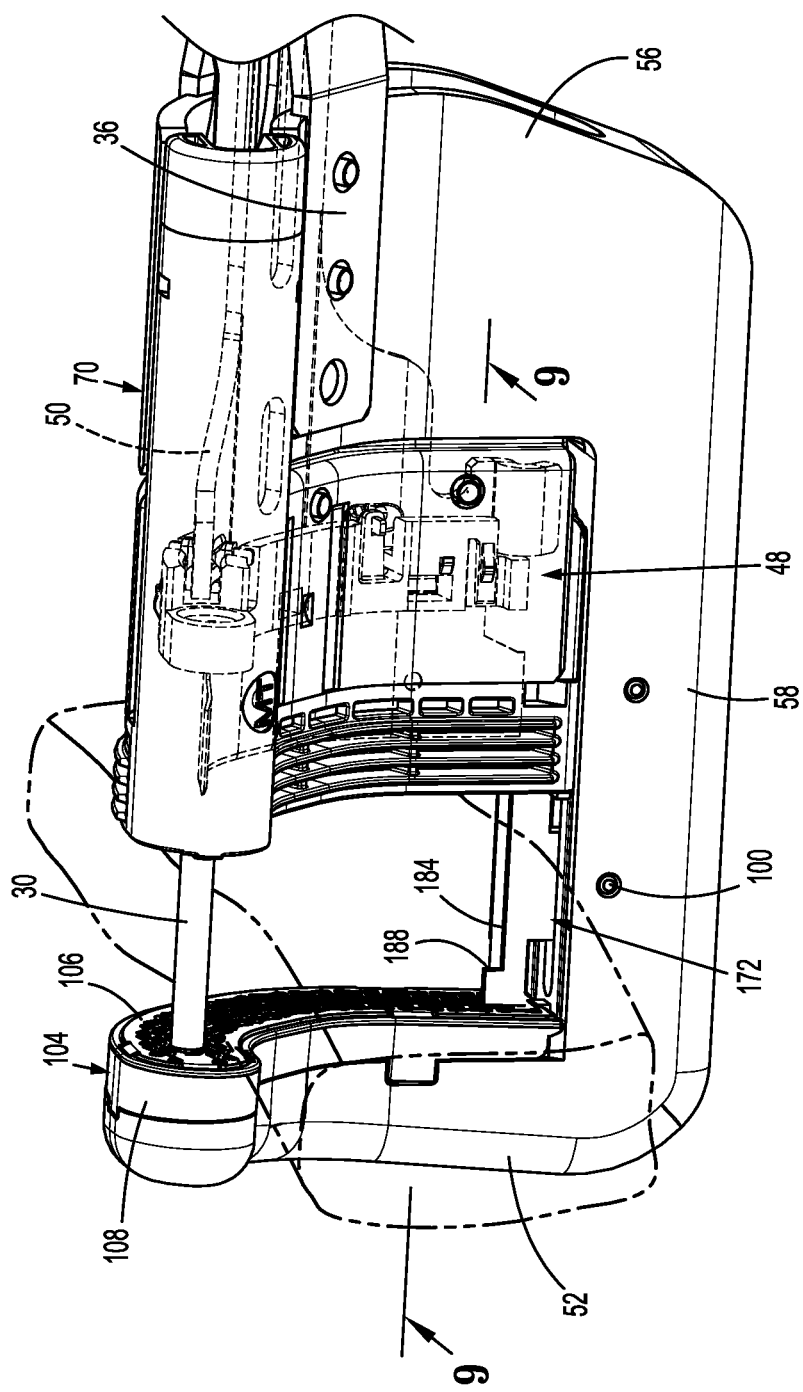
FIG. 8 is a side perspective view of a distal portion of the end effector of the stapling device shown in FIG. 1 with internal components of the end effector and the stapling device shown in phantom and the end effector in a pre-fired open position.

FIG. 4 illustrates the knife assembly 130 and the distal portion 72 of the thrust bar 50 with the thrust bar 50 coupled to the knife assembly 130. The knife assembly 130 includes a knife holder 150 and a cutting blade 152 that is secured to and extends distally from the knife holder 150. The cutting blade 152 includes a cutting edge 152a that is positioned on the distal end of the cutting blade 152 and wings 156 that are positioned on opposite sides of the cutting blade 152. The knife holder 150 includes a body 160 that defines a channel 162 that receives the distal portion 72 of the thrust bar 50 when the cartridge module 70 is inserted into the clamp slide assembly 48. The body 160 includes resilient fingers 164 that extend proximally from the body 160 of the knife holder 150. Each of the resilient fingers 164 includes a detent 164a that is received in an opening 166 defined in the distal portion 72 of the thrust bar 150 in snap-fit fashion when the cartridge module 70 is inserted into the curved pocket 66 (FIG. 2) of the clamp slide assembly 48.

FIGS. 3 and 5-7 illustrate a cutting blade guide assembly 170 that is supported on the longitudinal portion 54 of the end effector frame 52 and includes a guide member 172 and a biasing member 174. The guide member 172 includes a body 176 having a lower fin 178 and a guide portion 180 that extends distally of the lower fin 178. The lower fin 178 is received within the channel 94 (FIG. 3) formed in the longitudinal portion 58 of the end effector frame 52 and defines a longitudinal slot 182 that receives the pin 100 to secure the guide member 172 to the longitudinal portion 58 of the end effector frame 52. The longitudinal slot 182 in lower fin 178 of the guide member 172 allows the guide member 172 to move between retracted and advanced positions within the channel 94 along the longitudinal portion 58 of the end effector frame 52.

The body 176 of the guide member 172 defines a recess 184 that extends longitudinally along a portion of the guide member 172 and is defined by a lower guide wall 186 and a distal abutment surface 188. The guide portion 180 includes a pin portion 190 that is received within the bottom guide bore 88 (FIG. 3) of the distal transverse portion 54 of the end effector frame 52. In aspects of the disclosure, the pin portion 190 includes a rectangular portion 190a and a cylindrical portion 190b that extends distally from the rectangular portion 190a.

FIGS. 6-9 illustrate the end effector 16 with the clamp slide assembly 48 and the thrust bar 50 in their retracted positions and the cartridge module 70 spaced from the anvil assembly 104 in the open position. As illustrated, the guide member bore 88 is stepped and receives the biasing member 174 of the guide assembly 170. In some aspects of the disclosure, the biasing member 174 includes a coil spring that is positioned about the cylindrical portion 190b of the pin portion 190 of the guide member 172 between the rectangular portion 190 of the guide member 172 and a step 198 (FIG. 9) of the guide member bore 88. The biasing member 174 urges the guide member 172 towards its retracted position in which the pin portion 190 of the guide member 172 is received through the guide member openings 116 and 124 of the cut plate 108 and the anvil member 106, respectively, and extends partly into the guide member bore 88 of the distal transverse portion 54 of the end effector frame 52.

As described above, the knife assembly 130 is coupled to the distal portion 72 of the thrust bar 50. When the thrust bar 50 is in its retracted position, the knife assembly 130 is in its retracted position such that the cutting blade 152 of the knife assembly 130 is aligned with but spaced proximally of the recess 184 in the guide member 172. The lower wing 156 of the cutting blade 152 is spaced proximally of and aligned with the recess 184 in the guide member 172 when the knife assembly is in its retracted position and the cartridge module 70 is in the open position.

Figure 10:
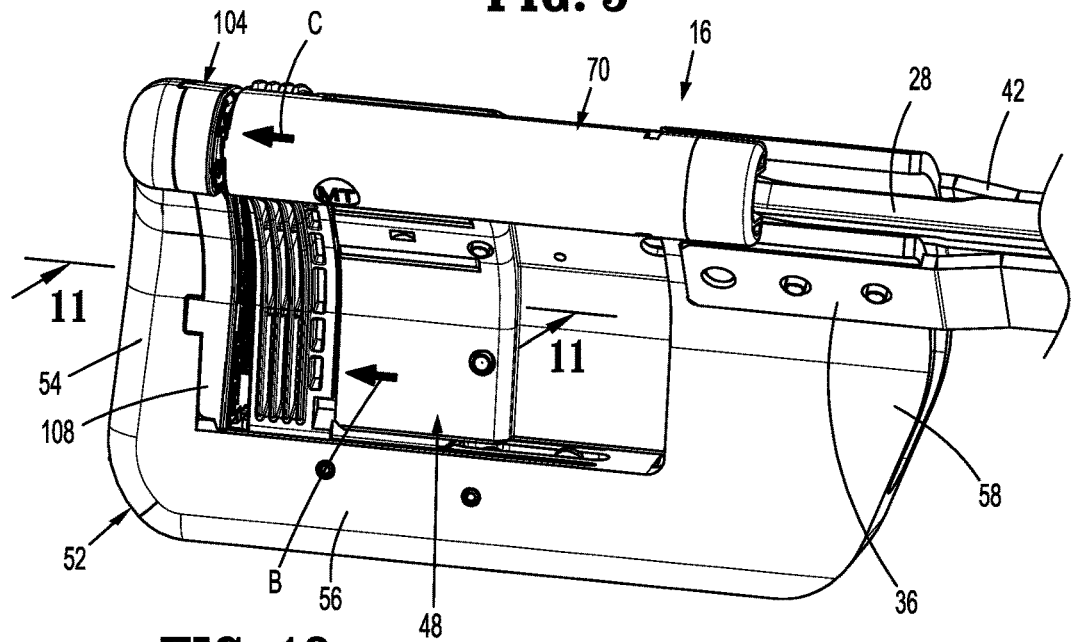
FIG. 10 is a side perspective view of the distal portion of the end effector of the stapling device shown in FIG. 1 with the end effector in a clamped position.
Figure 11:
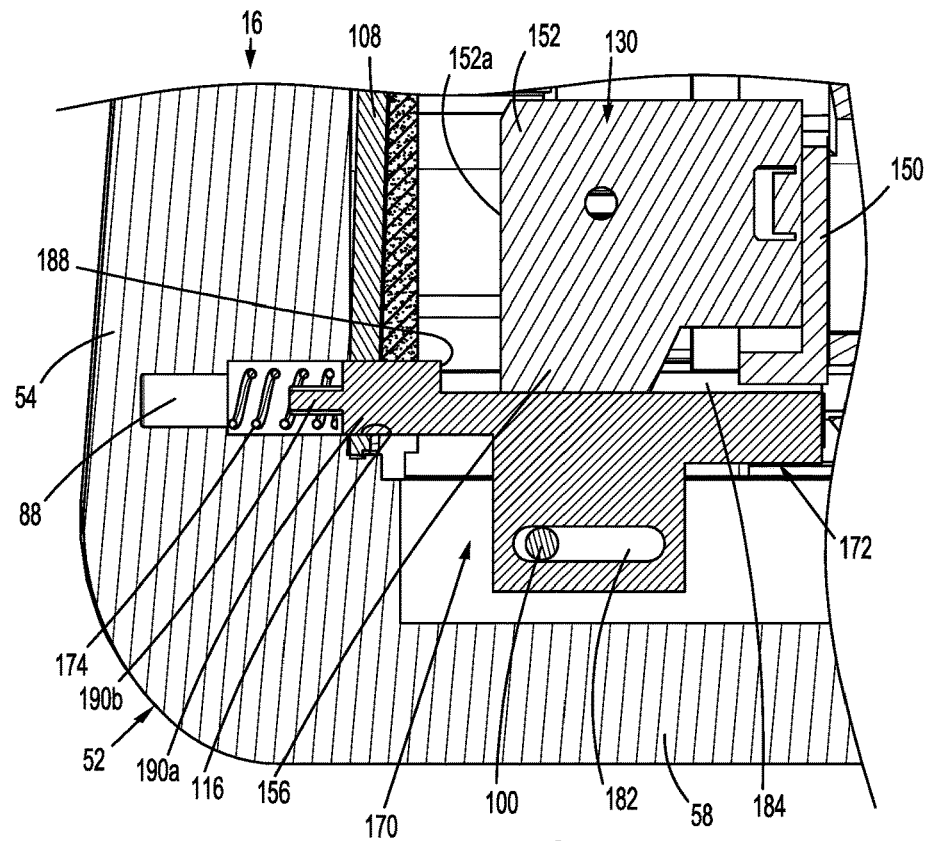
FIG. 11 is a cross-sectional view taken along section line 11-11 of FIG. 10.

FIGS. 10 and 11 illustrate the end effector 16 as the clamp slide assembly 48 is moved from its retracted position to its advanced position in the direction of arrow "B" in FIG. 10 to move the cartridge module 70 in the direction of arrow "C" in FIG. 10 from the open position to the clamped position. As the cartridge module 70 moves from the open position towards the clamped position, the lower wing 156 of the cutting blade 152 moves into and along the recess 184 of the guide member 172. Since the cutting blade 152 is positioned proximally of the abutment surface 188 of the guide member 172, the guide member 172 remains stationary as the cartridge module 70 moves to the clamped position. The biasing member 174 urges the guide member 172 towards its retracted position.

Figure 12:
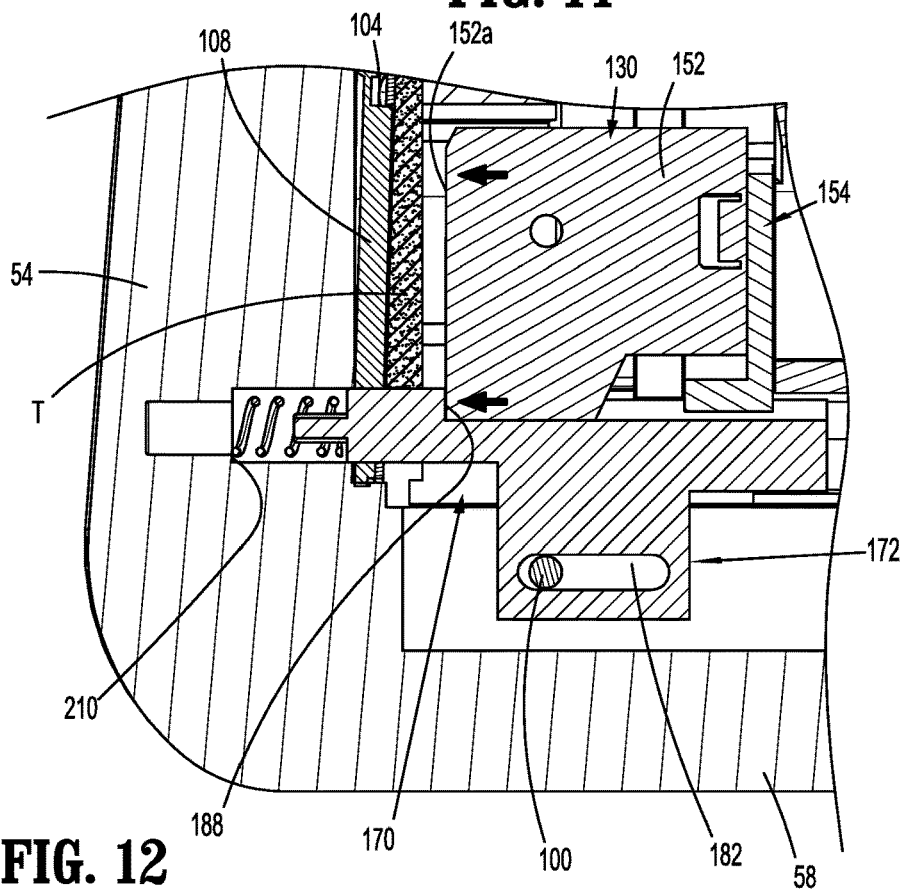
FIG. 12 is a side perspective view of the distal portion of the end effector of the stapling device shown in FIG. 1 with the end effector in a clamped and partially fired position.
Figure 13:
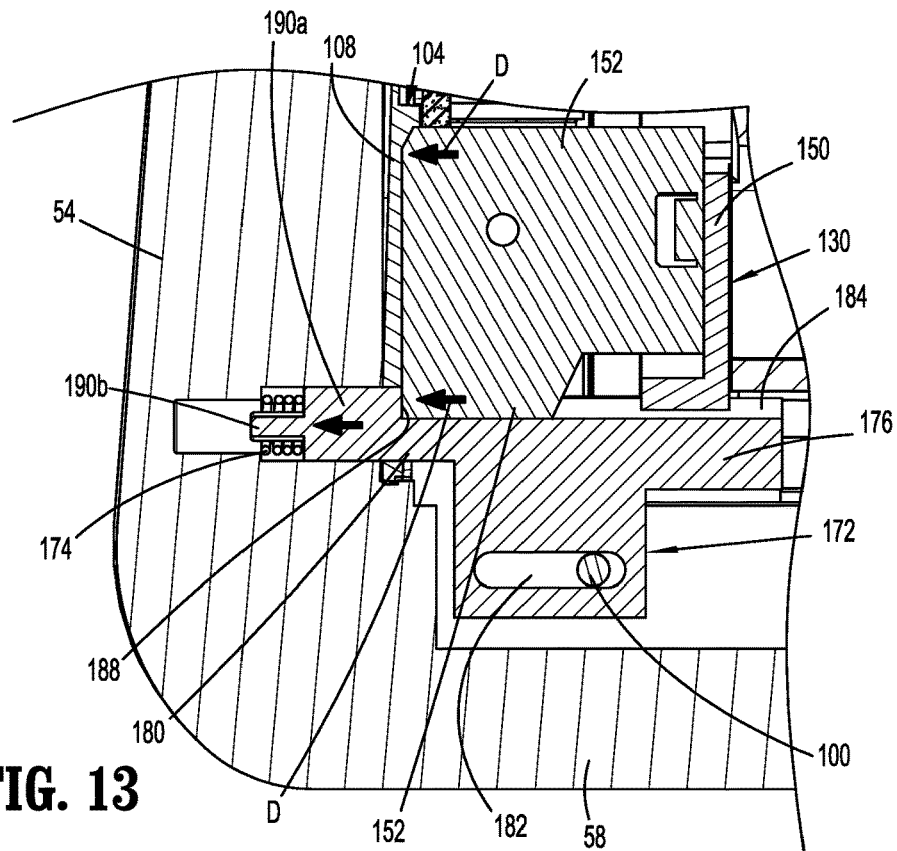
FIG. 13 is a side perspective view of the distal portion of the end effector of the stapling device shown in FIG. 1 with the end effector in a clamped and fully fired position.

FIGS. 12 and 13 illustrate a distal portion of the end effector 16 as the stapling device 10 (FIG. 1) is fired. When the movable trigger 22 is actuated, i.e., compressed towards the stationary handle 20 of the handle assembly 12, the thrust bar 50 (FIG. 4) is advanced from its retracted position to its advanced position to advance the knife assembly 130 in the direction indicated by arrows "D" in FIG. 13 to advance the cutting blade 152 into the cut plate 108 of the anvil assembly 104. When the wing 156 of the cutting blade 152 engages the abutment surface 188, continued advancement of the cutting blade 152 causes the guide member 172 of the guide assembly 170 to move distally with the cutting blade 152. As illustrated, the cutting blade 152 extends to a position below the guide member 172. The guide member 172 engages tissue "T" (FIG. 12) and prevents the tissue "T" from moving to a position outside of a path of travel of the cutting edge 152a of the cutting blade 152. This improves the likelihood that tissue is cleanly cut though even at the bottom end of the cutting blade 152, i.e., the end of the cutting blade 152 adjacent the longitudinal portion 58 of the end effector frame 52. The pin 100 which is fixedly secured to the longitudinal portion 58 of the end effector frame 52 and is received in the longitudinal slot 182 of the guide member 172 is positioned in a proximal portion of the longitudinal slot 182 when the knife assembly 130 is in its advanced position. When the knife assembly 130 is returned to its retracted position, the biasing member 174 returns the guide member 172 to its retracted position.

FIGS. 14-34 illustrate an alternate version of an end effector for a surgical stapling device including a guide assembly for improving the likelihood that tissue is cleanly cut at a bottom end of the end effector. The guide assembly described below differs from the guide assembly 170 (FIG. 3) described above in that unlike the guide assembly 170 which is secured to the end effector frame 52 (FIG. 3) and is reusable, the guide assembly described below forms part of a reload assembly and is disposable with the reload assembly.

Figure 14:
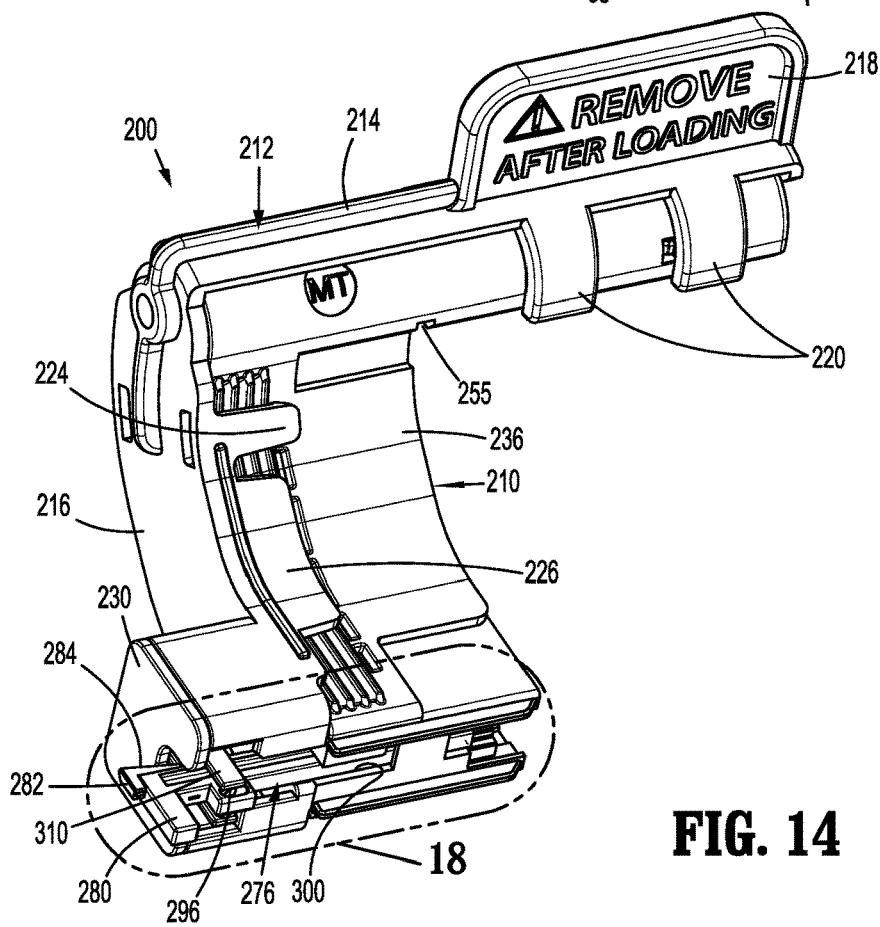
FIG. 14 is a side perspective view from the distal end of a reload assembly according to other aspects of the disclosure.

FIGS. 14 and 15 illustrate a reload assembly 200 according to aspects of the disclosure that includes a cartridge module 210 and a shipping cap 212. The shipping cap 212 is releasably coupled to the cartridge module 210 and includes a longitudinal portion 214 and a transverse portion 216. The longitudinal portion 214 includes a gripping tab 218 and resilient C-clips 220 that are spaced apart from each on the longitudinal portion 214. The C-clips 220 receive a portion of the cartridge module 210 to releasably secure the shipping cap 212 to the cartridge module 210. The transverse portion 216 of the shipping cap 212 extends transversely from a distal end of the longitudinal portion 214 and includes a cover plate 222 and tabs 224, 226 that extend proximally from the side edges of the cover plate 222. The tabs 224, 226 are positioned to engage side walls of the cartridge module 210 to help retain the shipping cap 212 on the cartridge module 210. The cover plate 222 includes a proximal surface 222a. The transverse portion 216 of the shipping cap 212 includes a surface 222a (FIG. 25) that faces the cartridge module 210. The transverse portion 216 of the shipping cap 212 includes a box-like housing 228 that is spaced from the longitudinal portion 214 and defines a cavity 228a that has an open distal end 228b. The open distal end 228a is covered by a cover plate 230 that defines a guide member slot 232.

The cartridge module 210 includes a cartridge body 236, an alignment pin assembly 238, a knife assembly 240, a pusher 242, and staples 244. The cartridge body 236 has a curved configuration and defines a cavity 246 (FIG. 21) that receives the knife assembly 240 and the pusher 242. The cartridge body 236 also defines a knife slot 248, staple receiving slots 250, an alignment pin opening 254, and a notch 255 (FIG. 14). The staple receiving slots 250 are positioned in rows on opposite sides of the knife slot 248 and are covered by the proximal surface 222a (FIG. 25) of the shipping cap 212 when the shipping cap 212 is coupled to the cartridge module 210. The cartridge body 236 includes a longitudinal portion 252 that is positioned on a first side of the cartridge body 236 and defines a bore (not shown) that receives the alignment pin assembly 238 such that an alignment pin 260 of the alignment pin assembly 238 is extensible through the alignment pin opening 254.

The alignment pin assembly 238 includes the alignment pin 260, a coupling member 262 that is secured to a proximal end portion of the alignment pin 260, and a biasing member 264. The biasing member 264 is positioned between a portion of the cartridge body 236 and the coupling member 262 to urge the alignment pin 260 to a retracted position recessed within the longitudinal portion 252 of the cartridge body 236. The longitudinal portion 252 of the cartridge body 236 has an open proximal end that is enclosed by a cover 266.

The knife assembly 240 includes a knife holder 268 and a cutting blade 270 that is secured to and extends distally from the knife holder 268. The knife holder 268 and the cutting blade 270 have curved configurations that correspond to the configuration of the cartridge body 236.

The pusher 242 defines a knife slot 242a (FIG. 21) that receives the cutting blade 270 of the knife assembly 240 and includes a plurality of fingers 274. Each of the fingers 274 is received within one of the staple receiving pockets 250 of the cartridge body 236 and supports a staple 244. The proximal portion of the pusher 242 is in abutting relation to the distal portion of the knife holder 268. The knife assembly 240 and the pusher 242 are movable within the cavity 246 of the cartridge body 236 between retracted and advanced positions to eject the staples 244 from the cartridge body 236 and to advance the cutting blade 270 through the knife slot 248 of the cartridge body 236.

Figure 17:
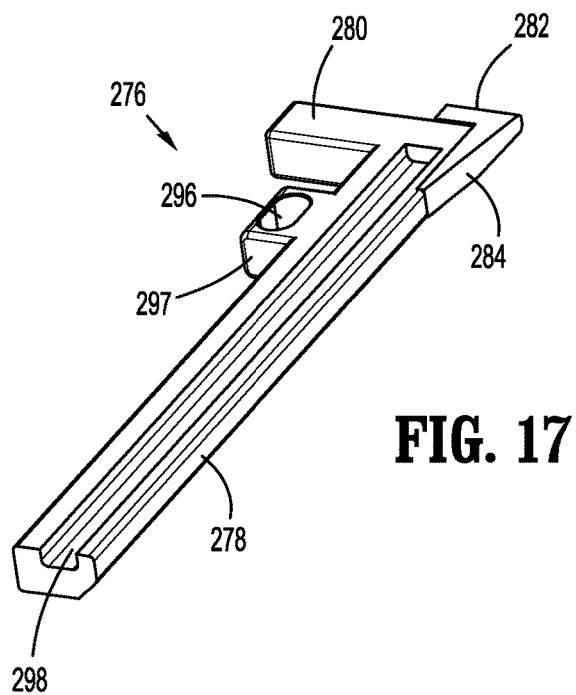
FIG. 17 is a side perspective view from the proximal end of the guide member shown in FIG. 16 assembled.
Figure 18:
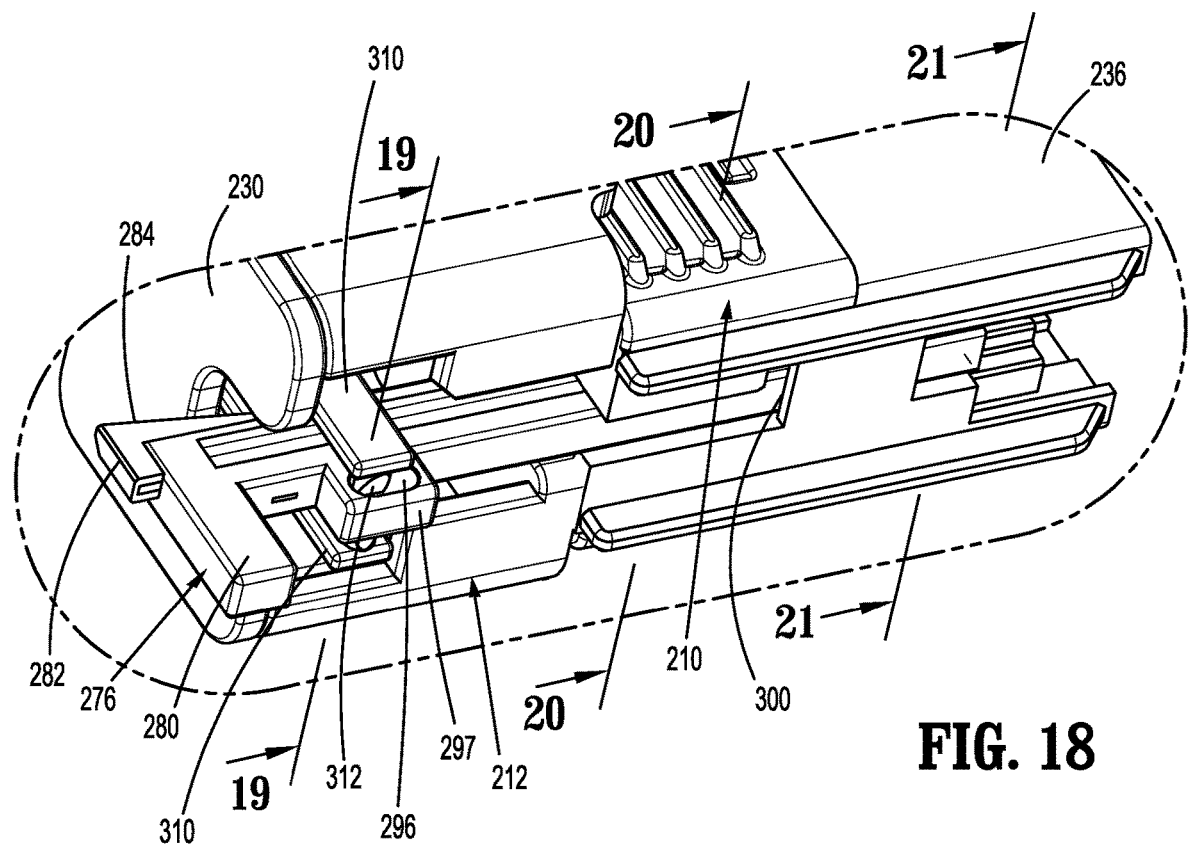
FIG. 18 is an enlarged view of the indicated area of detail shown in FIG. 14.
Figure 19:
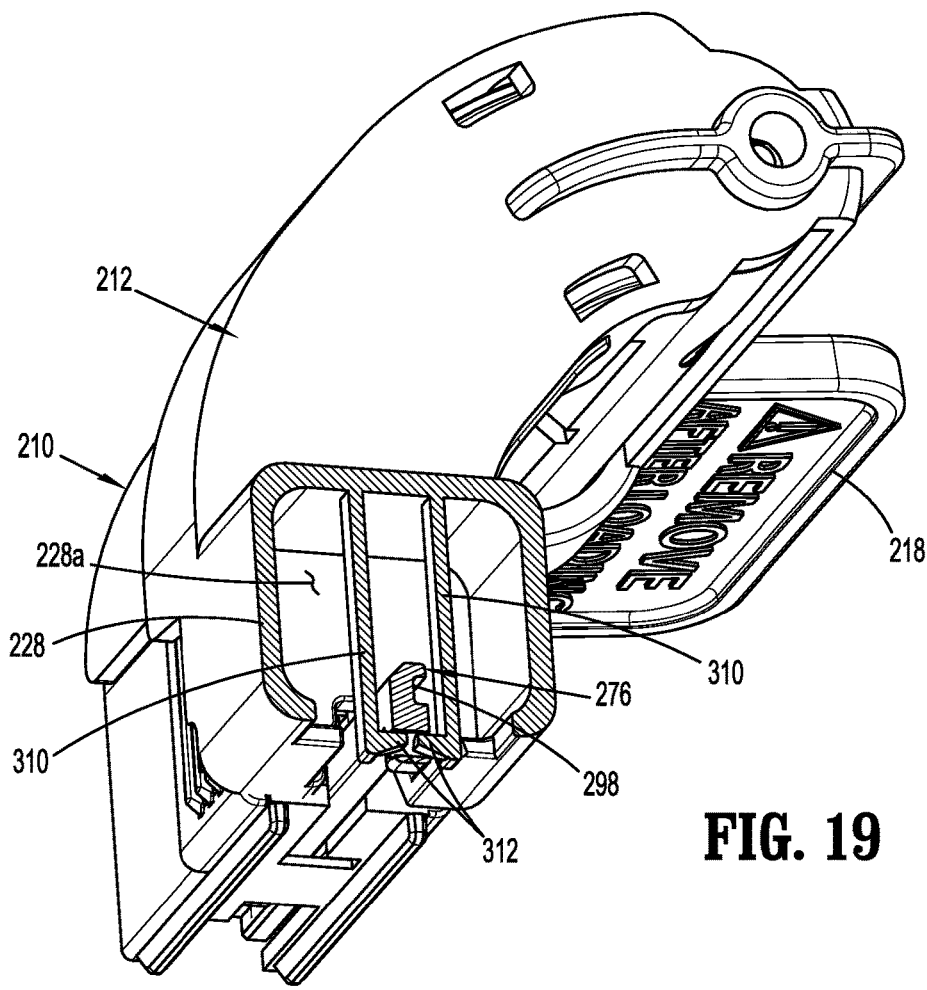
FIG. 19 is a cross-sectional view along section line 19-19 of FIG. 18.
Figures 20, 21:
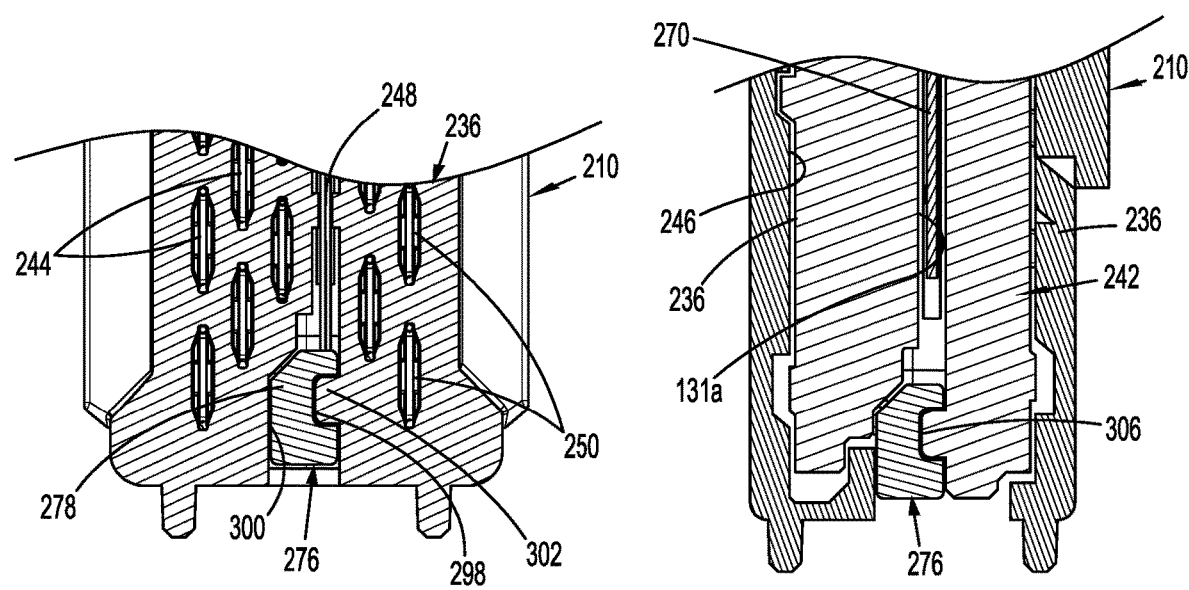
FIG. 20 is a cross-sectional view along section line 20-20 of FIG. 18.
FIG. 21 is a cross-sectional view along section line 21-21 of FIG. 18.

FIGS. 15-17 illustrate a guide member 276 of the cartridge module 210 that includes an elongate body portion 278, a finger 280, and a knife receiving member 282. The elongate body portion 278 and the finger 280 are integrally formed. The elongate body portion 278 has a proximal portion and a distal portion and the finger 280 extends outwardly from the distal portion of the elongate body portion 278. The knife receiving member 282 is formed of a soft material and is secured to and extends inwardly of the elongate body portion 278. In aspects of the disclosure, the knife receiving member 282 is formed of a soft plastic material that is over molded onto the distal portion of the elongate body portion 278 of the guide member 276 and includes an inner surface 284 that is angled inwardly into a path of the cutting blade 270 (FIG. 15). In some aspects of the disclosure, the distal portion of the elongate body portion 278 defines an opening 286 and includes a rib 288. When the knife receiving portion 282 is over molded onto the distal portion of the elongate body portion 278, the knife receiving portion 282 defines a slot 290 that receives the rib 288 and includes a transverse member 292 that is received in the opening 286 to secure the knife receiving portion 282 onto the elongate body portion 278. The distal portion of the elongate body portion 278 of the guide member 276 also defines an elongate through bore 296 and an elongate channel 298. The elongate bore 296 is formed in a downwardly positioned extension 297 of the elongate body portion 278.

FIGS. 18-22 illustrate the guide member 276 positioned within the cartridge body 236 of the cartridge module 210 and secured to the shipping cap 212. The cartridge module 210 defines a channel 300 that extends longitudinally through a second side of the cartridge body 236 opposite to the longitudinal portion 252 and receives the guide member 276. The channel communicates with the cavity 246 defined by the cartridge body 236. The cartridge body 236 includes a longitudinally extending rib 302 (FIG. 20) that is received within the elongate channel 298 of the guide member 276 when the guide member 276 is received within the channel 300 of the cartridge module 210. In some aspects of the disclosure, the guide member 276 is frictionally retained within the channel 300 of the cartridge body 236.

As described above, the pusher 242 of the cartridge module 210 is received within the cavity 246 of the cartridge body 236 and is movable between retracted and advanced positions. The pusher 242 includes a longitudinally extending rib 306 (FIG. 21) that is received within the elongate channel 298 of the guide member 276 when the guide member 276 is received within the channel 300 of the cartridge module 210.

Figure 26:
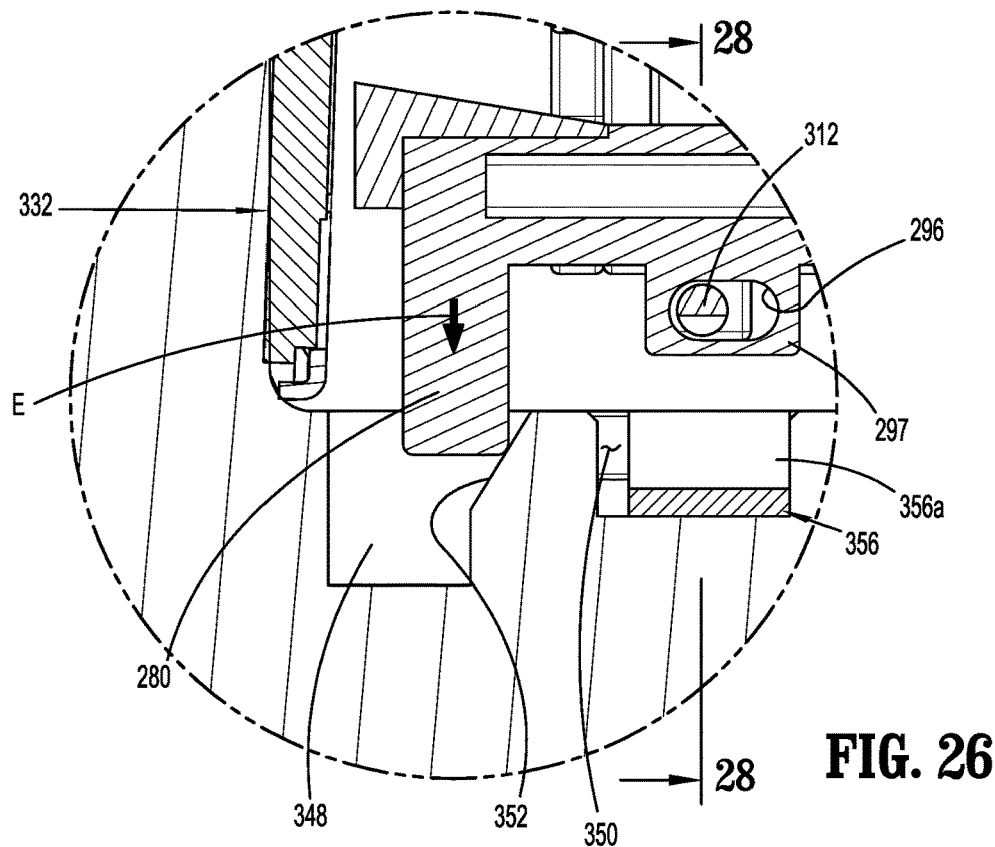
FIG. 26 is an enlarged view of the indicated area of detail shown in FIG. 24 as the reload assembly is loaded onto the clamp slide assembly of the stapling device.
Figure 27:
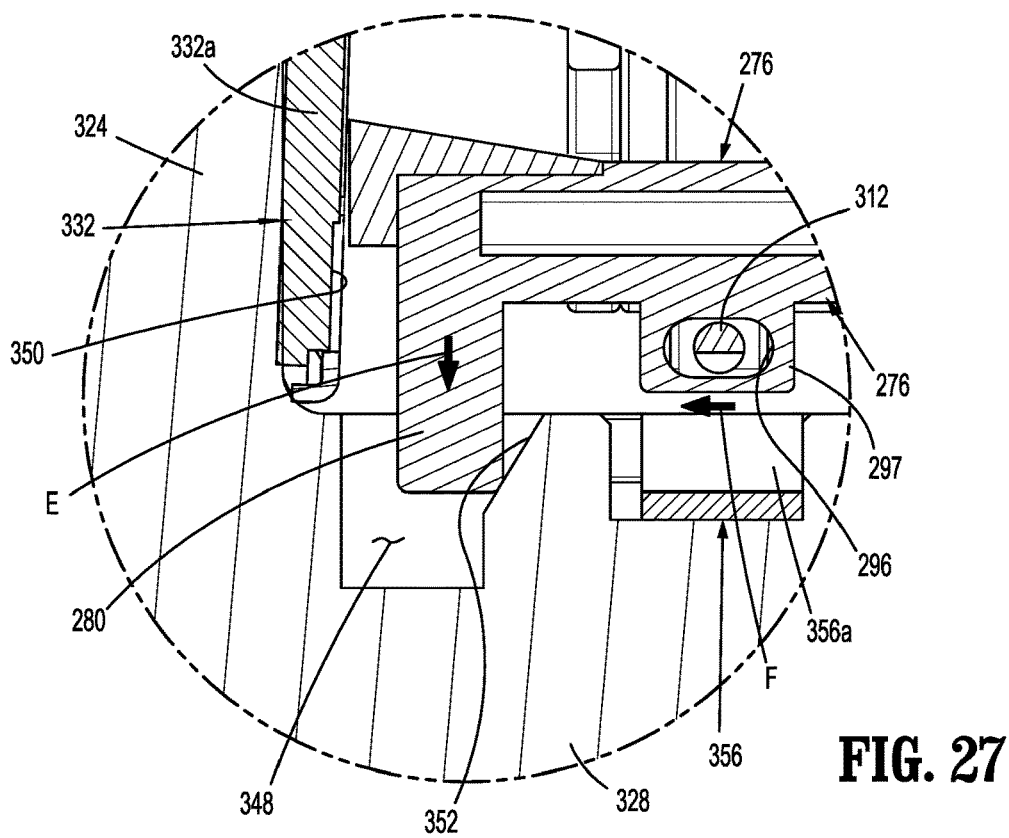
FIG. 27 is an enlarged view of the indicated area of detail shown in FIG. 24 as the reload assembly is loaded further onto the clamp slide assembly of the stapling device.

The box-like housing 228 (FIG. 19) of the transverse portion 216 of the shipping cap 212 includes flexible arms 310 that are supported in cantilevered fashion within the cavity 228a of the box-like housing 228. Each of the flexible arms 310 includes a protrusion 312 that is supported on an end portion of the respective flexible arm 310 and extends toward the other of the flexible arms 310. When the shipping cap 212 is coupled to the cartridge module 210, the protrusions 312 engage the guide member 276 and flex outwardly until the protrusions 312 become aligned with the through bore 296 of the extension 297 of the guide member 276. When the protrusions 312 become aligned with the through bore 296 of the guide member 276, the protrusions 312 snap into the through bore 296 to releasably secure the shipping cap 212 to the guide member 276. The protrusions 312 are smaller than the through bore 296 such that the protrusions 312 can move longitudinally within the through bore 296. When the shipping cap 212 is coupled to the cartridge module 210, before the cartridge module 210 is loaded onto a stapling device 10 (FIG. 1), the protrusions 312 are positioned in a distal end of the through bore 196 (FIG. 26).

Figure 23:
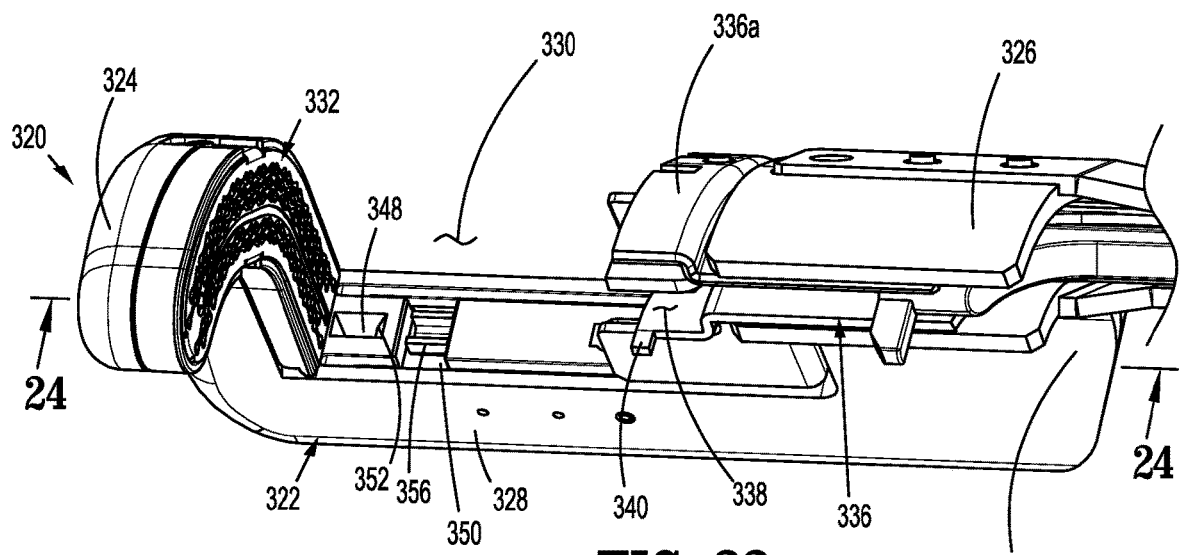
FIG. 23 is a side perspective view of an alternate version of the end effector of the stapling device shown in FIG. 1 with the reload assembly removed from the clamp slide assembly of the stapling device.
Figure 30:
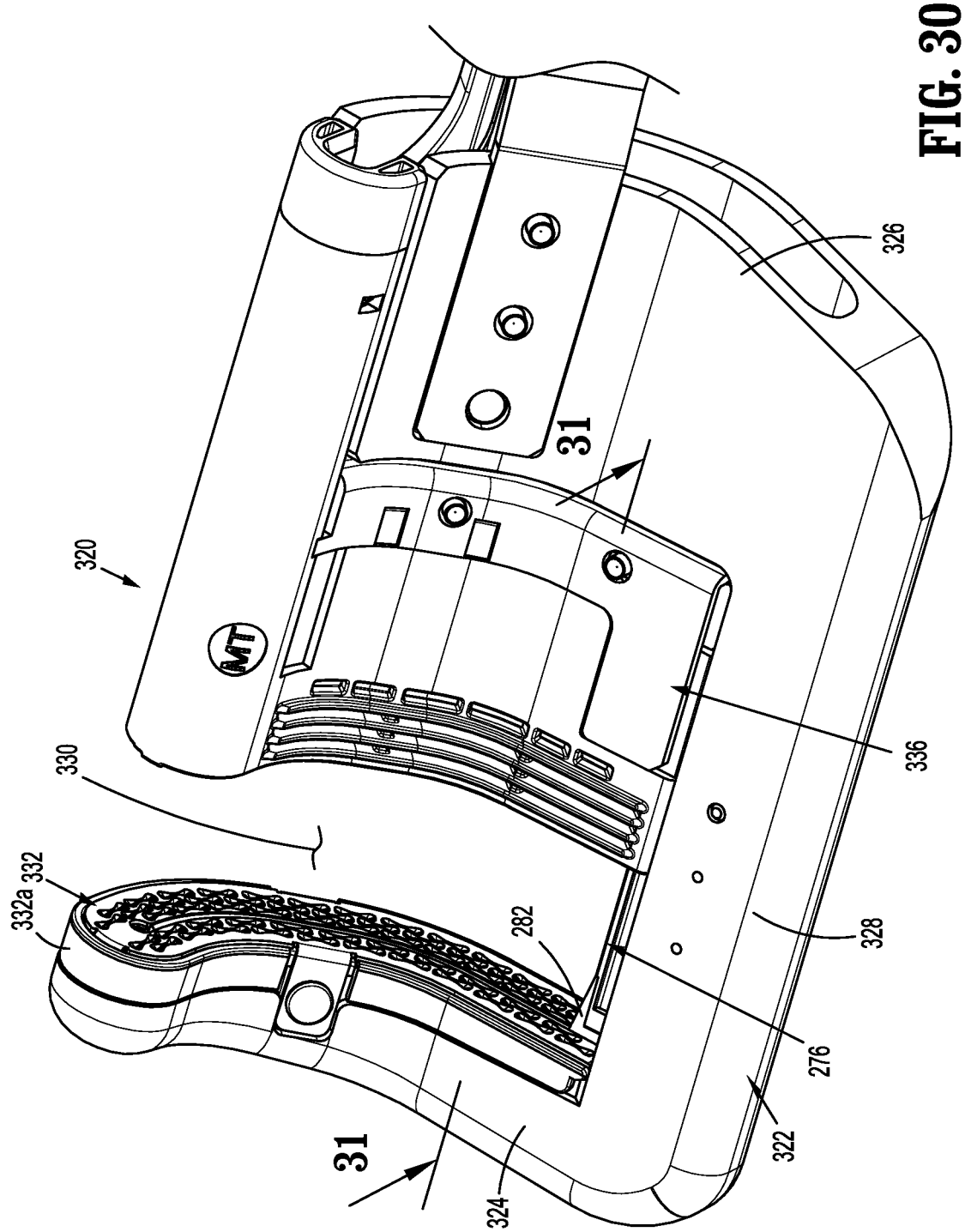
FIG. 30 is a side perspective view of the end effector of the stapling device shown in FIG. 1 with the cartridge module in an unclamped position.
Figure 31:
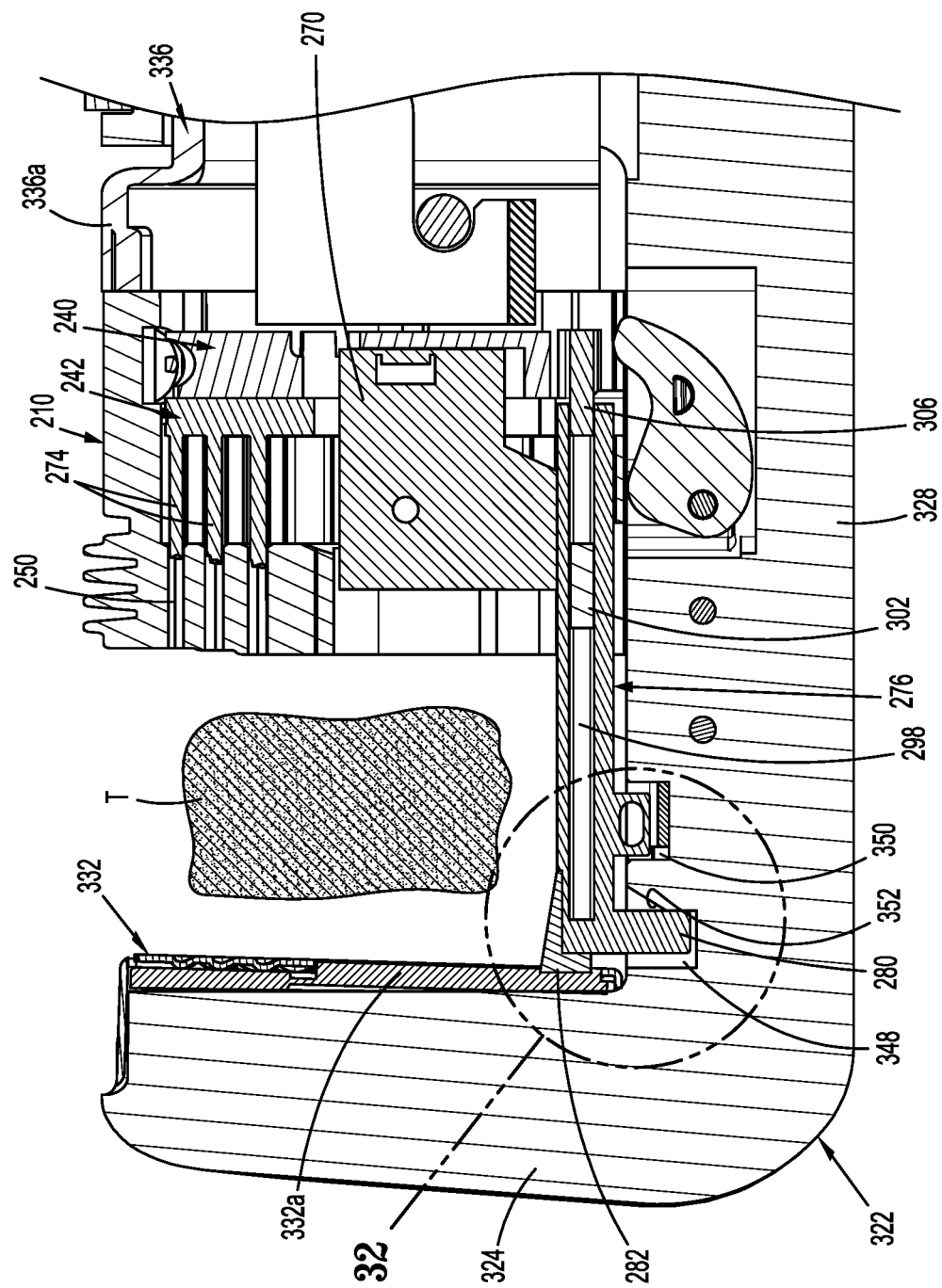
FIG. 31 is a cross-sectional view taken along section line 31-31 of FIG. 30.

FIGS. 23 and 24 illustrate an alternate version of the end effector of the stapling device 10 (FIG. 1) (with the cartridge module 210 removed) shown generally as end effector 320 (FIG. 30). The end effector 320 is like the end effector 16 described above and includes an end effector frame 322 that has a U-shaped configuration and includes a distal transverse portion 324, a proximal transverse portion 326, and a longitudinal portion 328 that interconnects the distal transverse portion 324 and the proximal transverse portion 326. The distal and proximal transverse portions 324 and 326 are spaced from each other to define a recess 330 that is positioned between the distal and proximal transverse portions 324 and 326. In some aspects of the disclosure, the distal and proximal transverse portions 324 and 326 are curved along axes transverse to the longitudinal axis "X" (FIG. 1) of the elongate body 14 of the stapling device 10.

Alternately, the distal and proximal transverse portions 324 and 326 may be linear or comprised of a plurality of linear portions that are positioned at angles in relation to each other.

Figure 22:
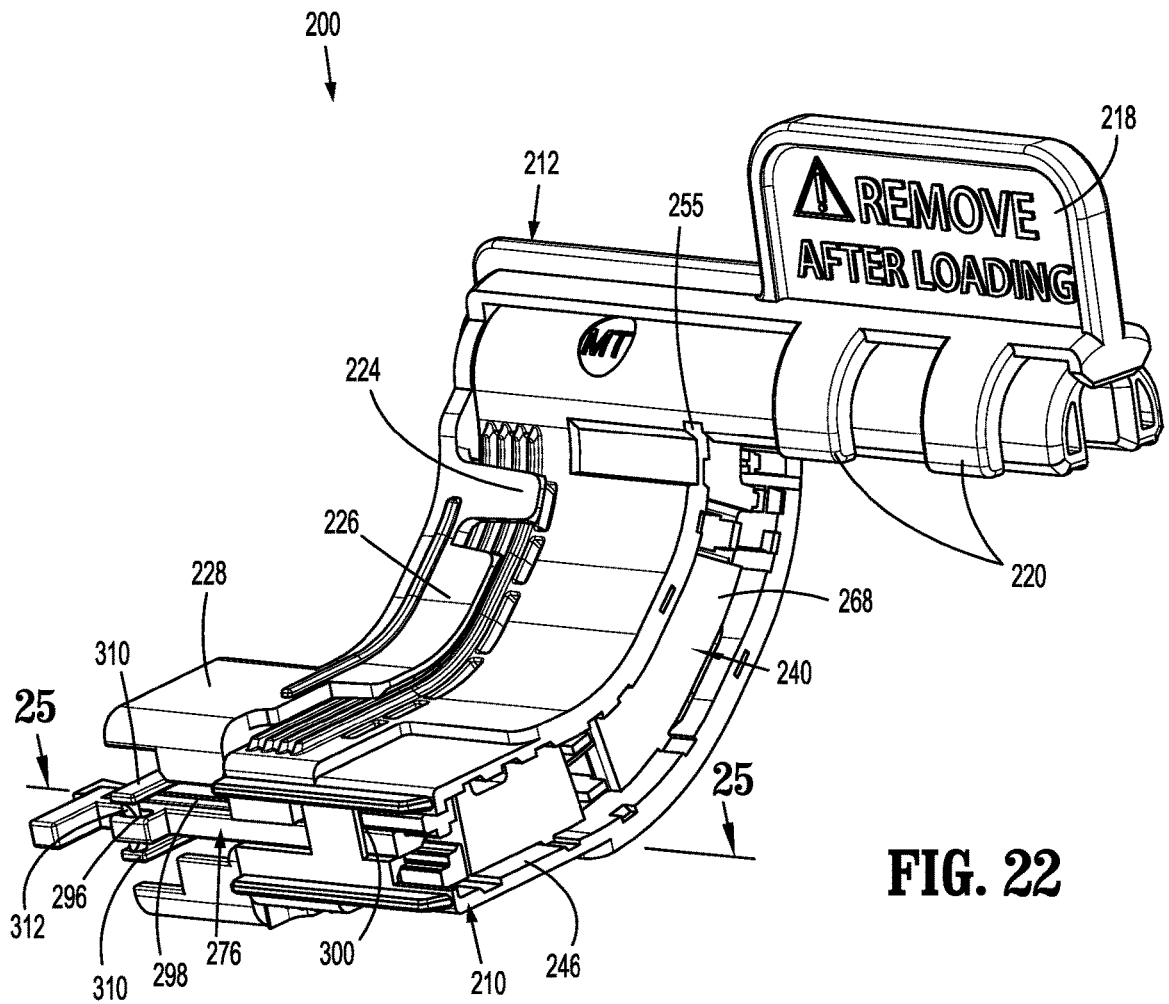
FIG. 22 is a side perspective view from the proximal end of the reload assembly shown in FIG. 14.

The distal transverse portion 324 of the end effector frame 322 supports an anvil assembly 332 which is like anvil assembly 104 (FIG. 23) described above and will not be described in further detail herein. A clamp slide assembly 336 includes a distal portion 336a (FIG. 3) that defines a curved pocket 338 (FIG. 23) that is configured to receive the cartridge module 210 (FIG. 22). The distal portion 336a of the clamp slide assembly 336 is positioned distally of the proximal transverse portion 326 of the end effector frame 322 within the recess 330 of the end effector frame 322 and includes a radially extending tab 340 (FIG. 23). The clamp slide assembly 336 is movable between retracted and advanced positions to move the cartridge module 210 in relation to the anvil assembly 332 within the recess 330 defined by the end effector frame 322 between spaced and clamped positions.

The thrust bar 342 includes a distal portion 344 (FIG. 24) that is positioned within the curved pocket 338 defined by the distal portion 336a of the clamp slide assembly 336. When the cartridge module 210 (FIG. 22) is inserted into the curved pocket 338 of the clamp slide assembly 336, the distal portion 344 of the thrust bar 342 engages the knife assembly 240 (FIG. 15) of the cartridge module 210 such that movement of the thrust bar 342 from its retracted position to its advanced position advances the knife assembly 240 and the pusher 242 (FIG. 15) to eject the staples 244 from the cartridge module 210 and cut tissue clamped between the anvil assembly 332 and the cartridge module 210.

The longitudinal portion 328 of the end effector frame 322 defines a distal bore 348 and a proximal bore 350. The distal bore 348 defines an angled proximal cam surface 352. The proximal bore 350 includes an insert plate 356 that is configured to engage the flexible arms 310 of the shipping cap 212 when the reload assembly 200 (FIG. 22) is loaded onto the clamp slide assembly 336 as described in further detail below. In some aspects of the disclosure, the insert plate is U-shaped and includes spaced side walls 356a.

Figure 32:
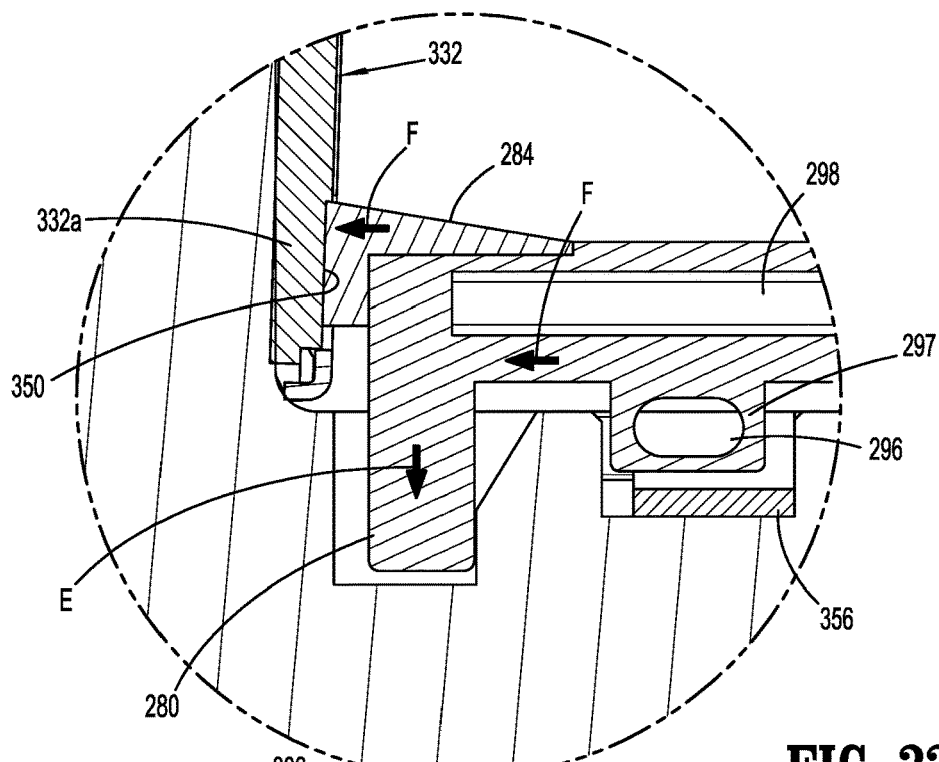
FIG. 32 is an enlarged view of the indicated area of detail shown in FIG. 31.

FIGS. 25-32 illustrate the reload assembly 200 as the reload assembly 200 is loaded onto the clamp slide assembly 336 of the stapling device. When the reload assembly 200 is slid into the curved pocket 338 of the clamp slide assembly 336 (FIG. 23) in the direction indicated by arrow "E" in FIGS. 26 and 27, the finger 280 of the guide member 276 of the cartridge module 210 engages the angled cam surface 352 that defines the distal bore 348 in the longitudinal portion 328 of the end effector frame 322. As the finger 280 moves along the angled cam surface 352, the guide member 276 is cammed distally in the direction of arrow "F" towards and into engagement with the anvil assembly 332. The protrusions 312 on the flexible arms 310 of the shipping cap 212 move from a distal end of the elongate bore 296 in the extension 297 of the guide member 276 to a proximal end of the elongate bore 296. When the reload assembly 200 is fully received within the curved pocket 338 in the distal portion 336a of the clamp slide assembly 336, the knife receiving member 282 of the guide member 276 is received within a recess 351 defined in a cut plate 332a of the anvil assembly 332 (FIG. 32). In addition, the tab 340 (FIG. 23) of the clamp slide assembly 336 is received within the notch 255 (FIG. 22) of the cartridge body 236.

Figure 29:
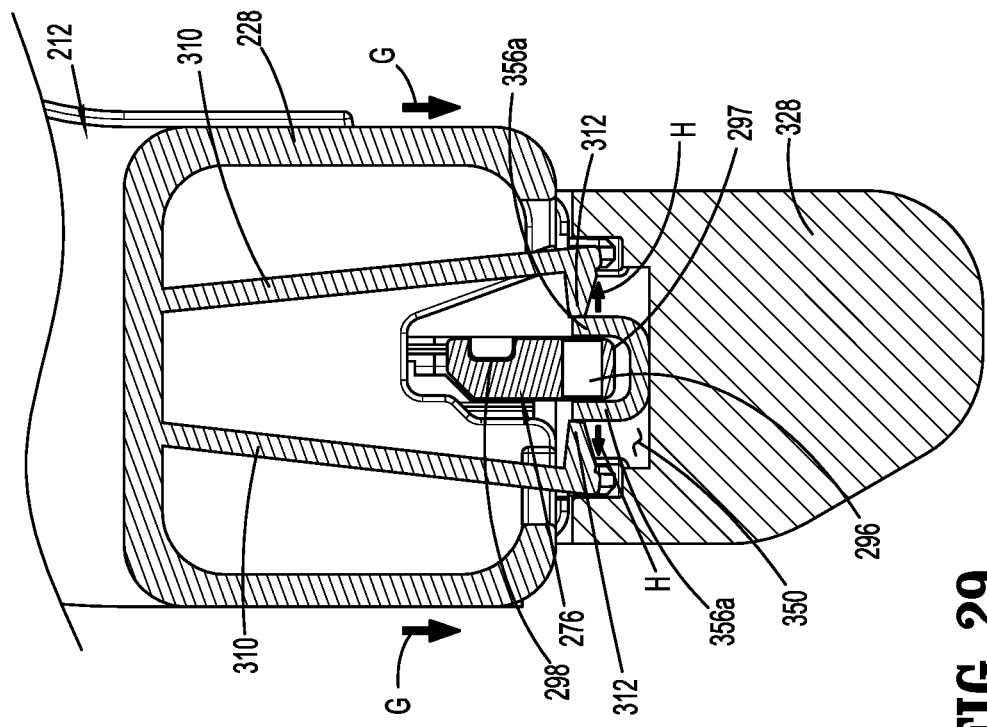
FIG. 29 is a cross-sectional view along section line 28-28 of FIG. 26 with the reload assembly loaded onto the clamp slide assembly of the stapling device.
Figure 28:
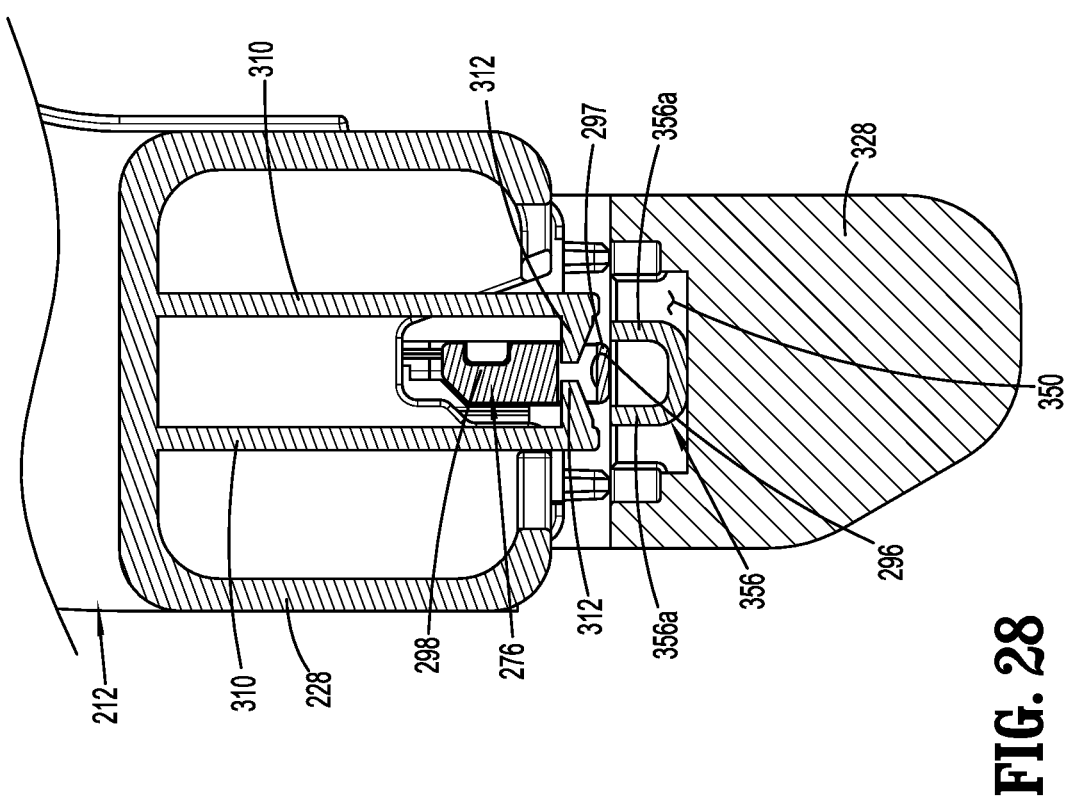
FIG. 28 is a cross-sectional view along section line 28-28 of FIG. 26 as the reload assembly is loaded onto the clamp slide assembly of the stapling device.

As the reload assembly 200 is loaded into the curved pocket 338 (FIG. 23) of the clamp slide assembly 336, the extension 297 defining the elongate bore 296 moves into the proximal bore 350 of the longitudinal portion 328 of the end effector frame 322 in the direction indicated by arrows "G" in FIG. 29 such that the flexible arms 310 of the shipping cap 212 engage the insert member 256. When the flexible arms 310 of the shipping cap 212 engage the insert member 256, the flexible arms 310 are cammed outwardly in the direction indicated by arrows "H" in FIG. 29 to remove the protrusions 312 from the elongate bore 296 of the shipping cap 212. When the protrusions 312 of the flexible arms 310 are removed from the elongate bore 296, the shipping cap 212 can be removed from the cartridge module 210.

Figure 33:
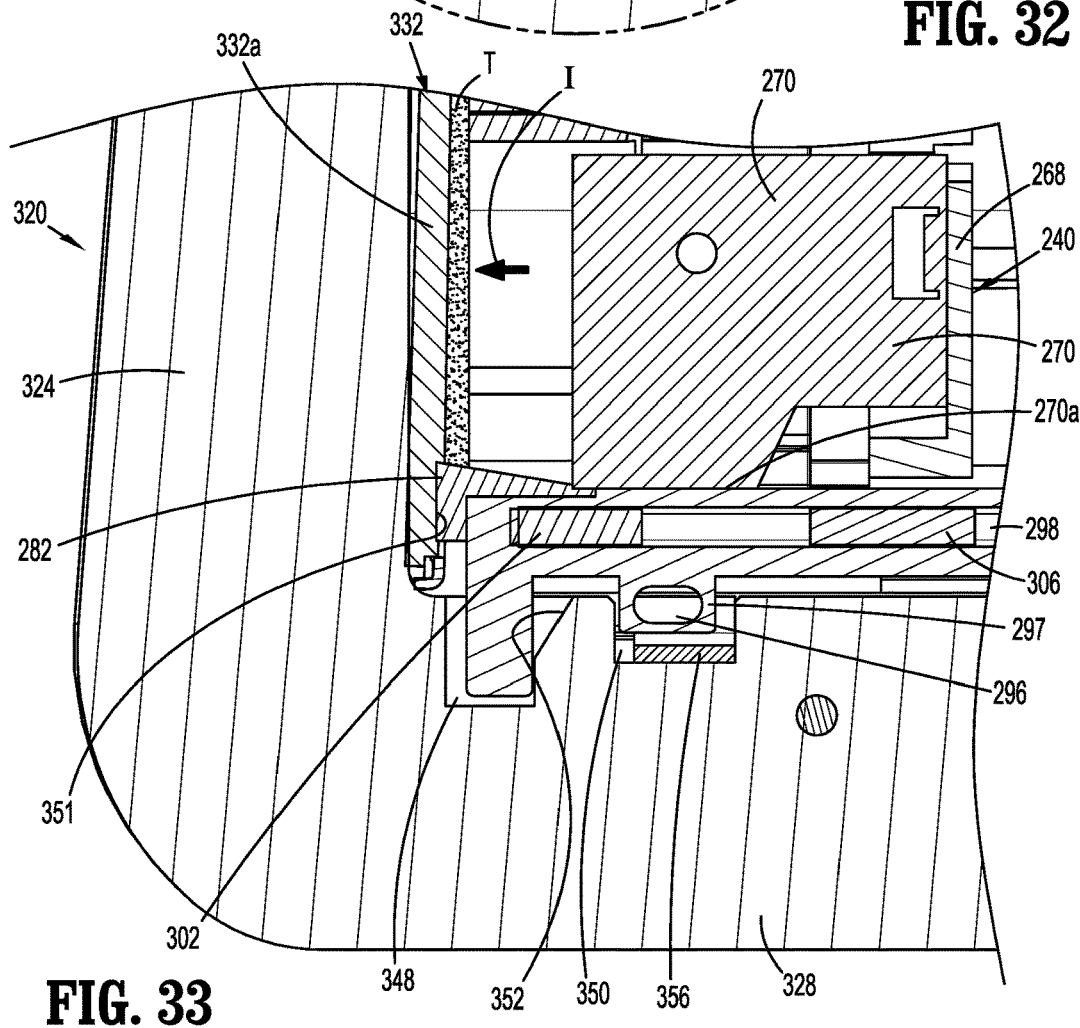
FIG. 33 is an enlarged cross-sectional view of a portion of the end effector shown in FIG. 30 as the stapling device is being fired.
Figure 34:
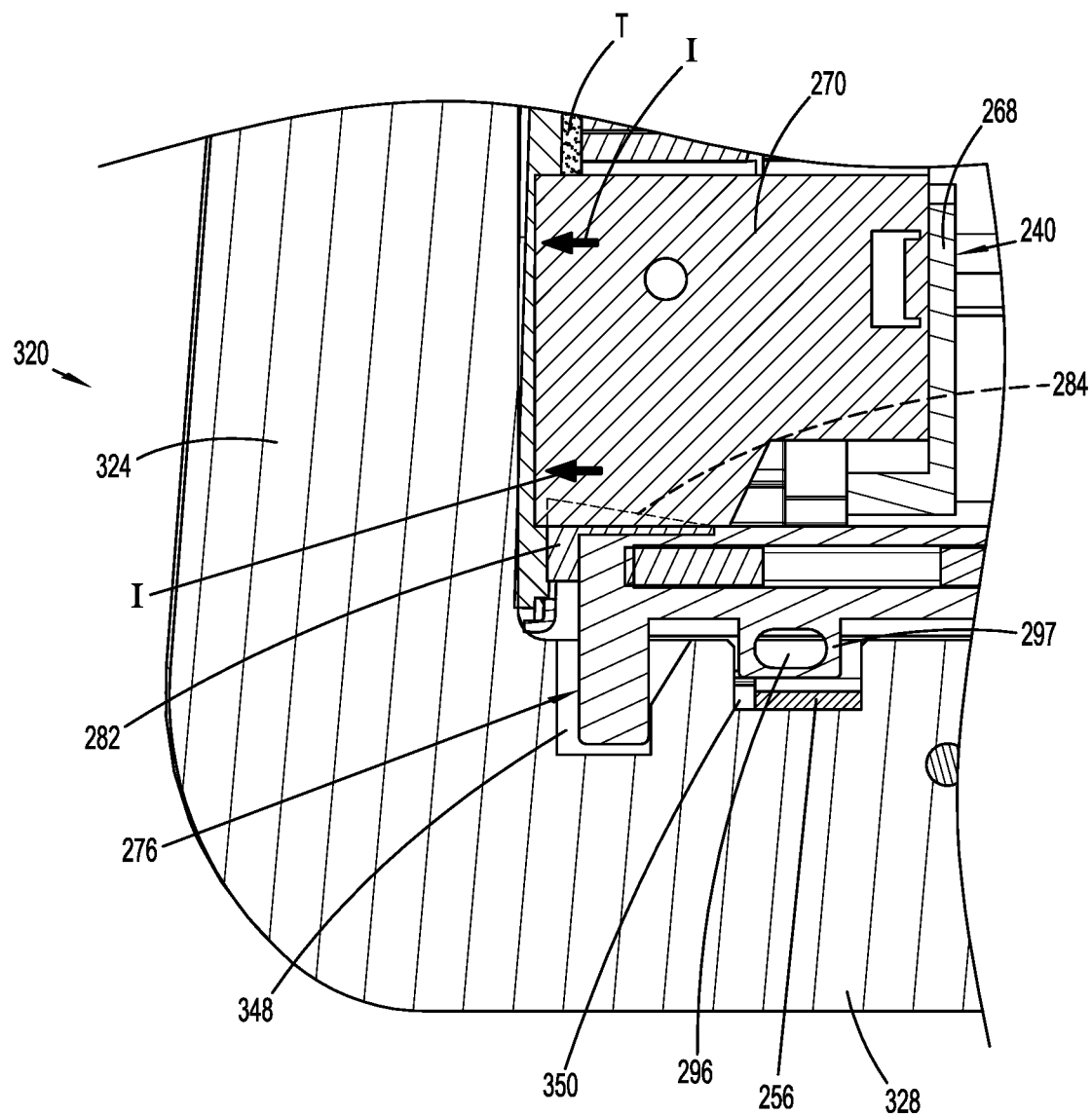
FIG. 34 is an enlarged cross-sectional view of a portion of the end effector shown in FIG. 30 after the stapling device has been fired.

FIGS. 33 and 34 illustrate a portion of the end effector 320 as the stapling device 10 (FIG. 1) is fired. When the stapling device 10 is fired, the knife assembly 240 is advanced in the direction indicated by arrows "I" within the cartridge body 236 of the cartridge module 210. As the knife assembly 240 is advanced within the cartridge body 236, the lower side edge 270a of the cutting blade 270, which may be in the form of a wing, moves along the guide member 276 and eventually cuts through the knife receiving member 282 of the guide member 276. As described above, the knife receiving member 282 is angled upwardly in the distal direction such that the cutting blade 270 cuts progressively through a greater thickness of the knife receiving member 282 as the cutting blade 270 moves to its fully advanced position. Engagement between the cutting blade 270 and the guide member 276 ensures that tissue "T" clamped between the anvil assembly 232 and the cartridge module 210 remains in the path of the cutting blade 270 and is effectively cut through cleanly.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A stapling device comprising:
an elongate body having a proximal portion and a distal portion;
a clamp slide assembly having a distal portion that defines a pocket, the clamp slide assembly movable between retracted and advanced positions;
a thrust bar having a proximal portion and a distal portion; and
an end effector including:
a cartridge module releasably received within the pocket of the clamp slide assembly, the cartridge module including a cartridge body, a knife assembly, a pusher, and staples, the cartridge body defining a knife slot and staple receiving slots positioned on each side of the knife slot, each of the staple receiving slots receiving one of the staples, the knife assembly including a knife holder and a cutting blade, the pusher including fingers that are received in the staple receiving slots, the knife assembly and the pusher movable within a cavity of the cartridge body from retracted to advanced positions to eject the staples from the cartridge body and to advance the cutting blade from a position recessed within the cartridge body to a position extending from the knife slot of the cartridge body;

an end effector frame having a distal transverse portion, a proximal transverse portion, and a longitudinal portion interconnecting the distal and proximal transverse portions at spaced locations, the distal and proximal transverse portions defining a recess that receives the distal portion of the clamp slide assembly and the distal portion of the thrust bar, the longitudinal portion of the end effector frame having an inwardly facing surface that defines a channel that extends longitudinally along the inwardly facing surface;

a pin supported by the end effector frame and extending across the channel;

an anvil supported on the distal transverse portion of the end effector frame; and a guide assembly supported on the longitudinal portion of the end effector frame, the guide assembly including a guide member having a body, the body including a lower portion and a guide portion that extends distally of the lower portion, the lower portion received within the channel and defining a longitudinal slot through which the pin extends, the body defining a recess that is defined in part by an abutment surface that is aligned with the cutting blade, the guide member movable from a retracted position to an advanced position in response to movement of the knife assembly from its retracted position to its advanced position.

2. The stapling device of claim 1, wherein the guide assembly includes a biasing member that urges the guide member towards its retracted position.

3. The stapling device of claim 2, wherein the distal transverse portion defines a bore that receives the guide portion of the guide member.

4. The stapling device of claim 3, wherein the biasing member is received within the bore in the distal transverse portion of the end effector frame.

5. The stapling device of claim 4, wherein the guide portion of the guide member incudes a rectangular portion and a cylindrical portion that extends distally from the rectangular portion, the biasing member positioned about the cylindrical portion and engaged with the rectangular portion.

6. The stapling device of claim 1, wherein the thrust bar is configured to couple to the knife holder when the cartridge module is received within the pocket of the clamp slide assembly.

7. The stapling device of claim 1, wherein the cartridge module and the end effector frame have curved configurations.

8. The stapling device of claim 1, further including a handle assembly, the elongate body extending distally from the handle assembly.

9. An end effector comprising:
an end effector frame including a distal transverse portion, a proximal transverse portion, and a longitudinal portion interconnecting the distal and proximal transverse portions at spaced locations, the distal and proximal transverse portions defining a recess, and the distal transverse portion defining a bore, and with the longitudinal portion of the end effector frame having an inwardly facing surface that defines a channel that extends longitudinally along the inwardly facing surface;

a guide assembly supported on the longitudinal portion of the end effector frame, the guide assembly including a guide member having a body, the body including a lower portion and a guide portion that extends distally of the lower portion and received by the bore, the lower portion received within the channel in the longitudinal portion of the end effector frame, the body defining a recess that is defined in part by an abutment surface that is aligned with a cutting blade of a cartridge module, the guide member movable from a retracted position to an advanced position along the longitudinal portion of the end effector frame; and a biasing member urging the guide member toward the retracted position.

10. The end effector of claim 9, wherein the biasing member is received within the bore in the distal transverse portion of the end effector frame.

11. The end effector of claim 10, wherein the guide portion of the guide member incudes a rectangular portion and a cylindrical portion that extends distally from the rectangular portion, the biasing member positioned about the cylindrical portion and engaged with the rectangular portion.

12. The end effector of claim 9, wherein the distal and proximal transverse portions of the end effector frame have curved configurations.

13. The end effector of claim 9, wherein the lower portion of the guide member defines a longitudinal slot and the longitudinal portion of the end effector frame supports a pin that extends across the channel in the longitudinal portion and through the longitudinal slot in the lower portion of the guide member.

14. A surgical stapling device comprising:
an elongate body having a proximal portion and a distal portion;
a clamp slide assembly having a distal portion that defines a pocket, the clamp slide assembly movable between retracted and advanced positions;
a thrust bar having a proximal portion and a distal portion;
an end effector frame having a distal transverse portion, a proximal transverse portion, and a longitudinal portion interconnecting the distal and proximal transverse portions, the distal and proximal transverse portions spaced from each other to define a recess that receives the distal portion of the clamp slide assembly and the distal portion of the thrust bar, the longitudinal portion of the end effector frame having an inwardly facing surface that defines a distal bore, the distal bore defined in part by an angled camming surface;
an anvil supported on the distal transverse portion of the end effector frame; and
a reload assembly including:
a cartridge module including a cartridge body, a knife assembly, a pusher, staples, and a guide assembly, the cartridge body defining a knife slot, staple receiving slots positioned on each side of the knife slot, and a channel, each of the staple receiving slots receiving one of the staples, the knife assembly including a knife holder and a cutting blade, the pusher including fingers that are received in the staple receiving slots, the knife assembly and the pusher being movable within a cavity of the cartridge body from retracted to advanced positions to eject the staples from the cartridge body and to advance the cutting blade from a position recessed within the cartridge body to a position extending from the knife slot, the cartridge module releasably received within the pocket of the clamp slide assembly, the guide assembly including a guide member that is received within the channel of the cartridge body and movable from a retracted position to an advanced position, the guide member including an elongate body portion and a finger extending downwardly from the elongate body portion, wherein the finger is positioned to engage the angled camming surface on the longitudinal portion of the end effector frame when the cartridge module is loaded onto the clamp slide assembly, engagement between the finger and the angled camming surface moving the guide member from its retracted position to its advanced position; and a shipping cap supported on the cartridge module.

15. The stapling device of claim 14, wherein the guide assembly includes a biasing member that is positioned to urge the guide member to its retracted position.

16. The stapling device of claim 14, wherein the elongate body portion of the guide member includes an extension that extends downwardly from the elongate body portion and defines an elongate opening, and the shipping cap includes flexible arms, each of the flexible arms including a protrusion that is received within the opening in the extension to releasably secure the shipping cap to the cartridge module.

17. The stapling device of claim 16, wherein the longitudinal portion of the end effector frame defines a proximal bore that receives an insert plate, the flexible arms positioned to engage the insert plate when the cartridge module is loaded onto the clamp slide assembly to cam the flexible arms outwardly and remove the protrusions from the opening in the extension to facilitate removal of the shipping cap from the cartridge module.

* * * * *